US006731985B2

(12) United States Patent
Poore et al.

(10) Patent No.: US 6,731,985 B2
(45) Date of Patent: May 4, 2004

(54) IMPLANTABLE CARDIAC STIMULATION SYSTEM AND METHOD FOR AUTOMATIC CAPTURE VERIFICATION CALIBRATION

(75) Inventors: John W. Poore, South Pasadena, CA (US); Kerry Bradley, Glendale, CA (US); Laurence S. Sloman, West Hollywood, CA (US); Gene A. Bornzin, Simi Valley, CA (US); Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 302 days.

(21) Appl. No.: 09/981,555

(22) Filed: Oct. 16, 2001

(65) Prior Publication Data

US 2003/0083708 A1 May 1, 2003

(51) Int. Cl.[7] .............................................. A61N 1/362
(52) U.S. Cl. ....................................................... 607/28
(58) Field of Search ........................................ 607/4–28

(56) References Cited

U.S. PATENT DOCUMENTS 5,391,192 A * 2/1995 Lu et al.
2003/0050671 A1 * 3/2003 Bradley

OTHER PUBLICATIONS

Park, Euljoon, et al., A Detection Feature for Unipolar Ventricular AutoCapture™, St. Jude Medical, Single Page (Jun. 25, 2001).

* cited by examiner

Primary Examiner—Scott M. Getzow

(57) ABSTRACT

An implantable cardiac stimulation device and associated method perform an automatic calibration procedure for evaluating whether automatic capture verification can be recommended. The calibration procedure calculates and displays a number of variables for use by a medical practitioner in programming automatic capture operating parameters. An average paced depolarization integral (PDI) is determined from the cardiac signals following delivery of multiple stimulation pulse below and above capture threshold such that both pure lead polarization signals and evoked response signals may be analyzed. From the paced depolarization integral data, a capture threshold, a stimulation response curve, a minimum evoked response, a maximum lead polarization, an evoked response sensitivity, an evoked response safety margin, and a polarization safety margin are determined. Based on these variables, the calibration procedure determines if automatic capture verification can be recommended. If so, the stimulation device calculates a capture detection threshold. The automatic capture verification recommendation and the estimated calibration variables are displayed.

74 Claims, 17 Drawing Sheets

IMPLANTABLE CARDIAC STIMULATION SYSTEM AND METHOD FOR AUTOMATIC CAPTURE VERIFICATION CALIBRATION

FIELD OF THE INVENTION

The present invention relates to an implantable cardiac stimulation system using an automatic capture feature. More specifically, the present invention relates to an implantable cardiac stimulation system in which an external programmer controls an automatic capture calibration routine and displays pertinent information regarding the feasibility of performing automatic capture.

BACKGROUND OF THE INVENTION

Implantable cardiac stimulating devices including pacemakers, cardioverters and defibrillators, detect and treat incidents of cardiac arrhythmias. Such devices are coupled to a patient's heart through transvenous leads that are used to sense electrical signals from the heart and deliver both low voltage and high voltage electrical therapy to the heart. The device circuitry generally includes sensing circuitry for sensing cardiac electrical activities in order to detect intrinsic electrical depolarizations of the cardiac tissue that cause contraction of the respective heart chambers.

In the atria, detection of a P-wave indicates atrial contraction, and in the ventricles detection of an R-wave, also known as a QRS complex, indicates ventricular contraction. If detection of an intrinsic P-wave or an R-wave does not occur within a given interval of time, generally referred to as the "escape interval," the heart rate is determined as being too slow. A stimulation pulse is then generated by the pacemaker circuitry and delivered to the appropriate heart chamber at the end of the escape interval in order to stimulate the muscle tissue of the heart to contract, thus maintaining a minimum heart rate. The duration of the escape interval corresponds to some base pacing rate, for example an escape interval of 1,200 msec would maintain a base pacing rate of 50 heart beats per minute.

The electrical depolarization caused by the delivery of a stimulation pulse is known as an "evoked response." An evoked response will only occur when the stimulating pulse is of sufficient energy to cause depolarization of the cardiac tissue, a condition known as "capture." The minimum stimulating energy required to capture a chamber of the heart is known as "threshold."

Modern pacemakers often include a feature known as "automatic capture." When the automatic capture feature is implemented, the pacemaker circuitry detects the evoked response following the delivery of a stimulation pulse in order to verify that capture has occurred. If no evoked response is detected, the stimulation pulse may have been of insufficient energy to capture the heart; therefore, a high-energy back-up pulse is quickly delivered to the heart in order to maintain the desired heart rate. A threshold detection algorithm is then invoked in order to re-determine what minimum energy is required to capture the heart.

The stimulating pulse energy is automatically adjusted to this new threshold value plus some safety margin. As long as an evoked response is detected following a stimulation pulse, that is, as long as capture is verified, pacing will continue at the set pulse energy.

Hence, the automatic capture feature improves pacemaker performance in at least two ways: 1) it verifies that the stimulation therapy delivered has been effective in causing the heart chamber activation, and 2) it improves battery energy longevity by determining the lowest stimulation energy needed to effectively capture the heart.

However, one problem with capture detection is that the signal sensed by the ventricular and/or atrial sensing circuits immediately following the application of a stimulation pulse may not be an evoked response. Rather, it may be noise, either electrical noise caused, for example, by electromagnetic interference (EMI), or myocardial noise caused by random myocardial or other muscle contractions (muscle "twitching"). Alternatively, the signal sensed by the ventricular and/or atrial sensing circuits may be a natural R-wave or P-wave that just happens to occur immediately following the application of a non-capturing stimulation pulse.

Another problematic condition is "fusion". Fusion occurs when a pacing pulse is delivered such that the evoked response occurs coincidentally with an intrinsic depolarization. The evoked signal may be absent or altered preventing correct capture detection by the pacemaker's capture detection algorithm. A loss of capture may be indicated when capture is in fact present, which is an undesirable situation that will cause the pacemaker to unnecessarily deliver a high-energy back-up pacing pulse and to invoke the threshold testing function in a chamber of the heart. Frequent delivery of back-up pacing pulses or execution of threshold tests defeats the purpose of the energy-saving features of autocapture. If fusion continues during a threshold test, the pacing energy output may be driven to a maximum level, quickly depleting the battery energy.

The incidence of fusion can be particularly problematic in patients with intermittent or intact atrio-ventricular conduction being treated by dual chamber pacing. In dual chamber pacing, both atrial and ventricular activity are monitored. A P-wave detected in the atria is followed by an AV/PV interval which is the desired delay between an atrial depolarization and a ventricular depolarization. If an intrinsic R-wave is not detected prior to expiration of the AV/PV delay, a Vpulse is delivered to pace the ventricles. Since the AV conduction time may vary, an intrinsically conducted R-wave may occur at different times and therefore may occur approximately the same time that a ventricular pacing pulse is delivered. Furthermore, the AV/PV interval may be programmed inappropriately leading to increased likelihood of fusion events. Fusion masquerading as loss of capture will cause the pacemaker to initiate frequent threshold tests and may drive the pacemaker to its maximum pacing output.

Yet another signal that interferes with the detection of an evoked response is associated with lead electrode polarization. Lead electrode polarization is caused by electrochemical reactions that occur at the lead/tissue interface due to the application of the electrical stimulation pulse across such interface. The lead polarization signal is a complex function of the lead materials, lead geometry, tissue impedance, stimulation energy, and many other variables.

The evoked response is monitored within 3 to 80 msec of the stimulation pulse. During the early portion of this time, the lead polarization signal voltage is still relatively high. In order to minimize lead polarization voltage, low polarization materials can be used in manufacturing the electrode. Still, since the evoked response and polarization signal occur simultaneously, if the polarization signal is very high, it may not be possible to reliably detect an evoked response. The result may be a false positive detection of the evoked response. Such false positive detection leads to a false capture indication, which, in turn, can lead to missed heartbeats, a highly undesirable situation.

Variation in the lead polarization signal can be significant from patient to patient depending on implanted lead configurations and other factors. Therefore, calibration methods are generally required to determine a threshold for detecting the evoked response and distinguishing it from the lead polarization signal.

Different parameters or characteristics of the evoked response have been proposed in automatic capture calibration and automatic capture detection schemes, including impedance change, voltage differential (dV/dt), signal polarity reversal, and peak negative amplitude.

Typically, evoked response sensing occurs between the tip and ring of a bipolar lead connected to the device sensing circuits. The evoked response may also be monitored by sensing between the ring electrode and device housing. In either event, a bipolar pacing lead has generally been required in order to detect the evoked response. These configurations have been selected since they reduce the likelihood of false positive capture detection. Such reduction is achieved by selecting a feature in the bipolar evoked response that is not strongly expressed in the polarization artifact. Alternatively, in the ring-case configuration, one of the pacing electrodes may be removed from the sensing circuit, thereby reducing the sensed polarization signal. This implies that these automatic capture schemes will not work with unipolar pacing leads.

Thus, in patients having unipolar leads implanted in conjunction with a cardiac stimulation device, the ability to reliably employ the automatic capture feature has been heretofore limited.

It would thus be desirable to provide the cardiac stimulation system with an automatic calibration routine that evaluates variables associated with the lead polarization signal and the evoked response signal, and, based on this evaluation, determines whether or not the automatic capture feature is recommended for a particular patient. In addition, it would be desirable to report these calibration variables to the physician to allow him or her to make informed decisions in enabling or disabling the automatic capture feature and, when enabled, to make an informed decision in selecting appropriate automatic capture operating parameters.

SUMMARY OF THE INVENTION

The present invention addresses this and other needs by providing an implantable cardiac stimulation system with an automatic capture calibration feature capable of automatically evaluating whether the automatic capture can be reliably performed using a unipolar electrode configuration, and further calculating and reporting calibration variables that can be used by a medical practitioner in programming automatic capture parameters. It should be understood that the calibration procedure of the present invention can alternatively be performed using leads with bipolar or multipolar electrode configurations.

The implementation of this calibration procedure in an external programmer in communication with an implanted stimulation device allows thorough testing and evaluation of stimulation response signals, and gives the opportunity to display pertinent information regarding the feasibility of the automatic capture feature to the physician.

The automatic calibration procedure of the present invention, which employs the "paced depolarization integral method calibration" or "PDI-method calibration", can be executed by an external programmer controlling certain operations of an implanted cardiac stimulation device. The calibration procedure includes the following steps: 1) automatic gain adjustment and fusion avoidance adjustment; 2) paced depolarization integral data collection and table creation; 3) capture threshold determination and stimulation response curve slope determination; 4) automatic capture recommendation and failure conditions reporting; and 5) reporting of calibration variable estimations.

When the automatic calibration procedure is initiated, the external programmer first adjusts the gain of the sensing circuit (or circuits) of the implanted stimulation device to achieve a desired maximum magnitude of sampled signals. If necessary, the programmer also recommends adjustment of pacer timing parameters in order to minimize the likelihood of fusion, such as increasing the base rate of the pacemaker, or shortening the AV and or PV intervals.

The programmer then collects data relating to the lead polarization signal and the evoked response signal following the delivery of a stimulation pulse by integrating a sampled cardiac EGM signal. In so doing, the programmer triggers the implanted stimulation device to deliver a given number of stimulation pulses at a several pulse amplitude settings over a specified range, including both supra-capture threshold amplitudes and sub-capture threshold amplitudes. The sensed cardiac signal is integrated in order to obtain the paced depolarization integral (or PDI) associated with each stimulation pulse. The values of the integrals obtained for a given number of stimulating pulses at each pulse amplitude are statistically evaluated, and the results are stored in memory. If inappropriate or insufficient results are obtained during this data collection and analysis, the physician is alerted that the calibration procedure cannot be run.

Based on the paced depolarization integral data collected, the capture threshold is determined, and the slope of the stimulation response curve (pulse amplitude versus paced depolarization integral) is calculated. Based on further mathematical analysis of the paced depolarization integral data, which in essence determines the margin for safely discriminating an evoked response signal from a lead polarization signal, the activation of the automatic capture feature would be determined to be either 'recommended' or 'not recommended.'

For either condition, a set of calibration variables are calculated and displayed, including minimum and maximum evoked response amplitudes, maximum polarization signal amplitude, evoked response sensitivity, and evoked response safety margin. Having this information, the medical practitioner can make informed decisions in programming the automatic capture feature of an implantable cardiac stimulation device.

Thus, one feature of the present invention is a calibration procedure that is executed by an external programmer controlling certain operations of the implanted stimulation device. Another feature of the present invention included in this calibration procedure is the ability to make gain adjustments or fusion avoidance adjustments to improve the ability of the calibration procedure in collecting sufficient and appropriate data.

A further feature of the present invention is the ability to sample and digitize a cardiac stimulation response signal. Yet another feature of the present invention is a method for integrating the sampled stimulation response signal during a defined response time window and relative to an integration baseline in order to obtain a paced depolarization integral.

Still another feature of the present invention is the performance of mathematical and statistical analyses of the paced depolarization integral data in order to determine the capture threshold and by what margin automatic capture can be reliably performed. A further feature is the calculation of estimations of certain variables pertinent to the performance of automatic capture. Another feature is a method for displaying calibration procedure failure conditions, an automatic capture recommendation, and automatic capture variable estimations.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As indicated earlier, the present invention relates to an automatic capture calibration procedure that automatically determines whether automatic capture is recommended in a given patient and calculates calibration variables to be used in selecting programmable parameters of the automatic capture feature. This procedure, which will be described in detail in conjunction with FIGS. 3 through 18, is intended for use in cardiac stimulation devices employing either unipolar or bipolar stimulation and unipolar sensing electrode configurations. The methods employed by these cardiac stimulation devices could be implemented in an external programmer. While these methods could be implemented in numerous cardiac stimulation devices, an exemplary stimulation device will now be described in conjunction with FIGS. 1 and 2.

Figure 1:
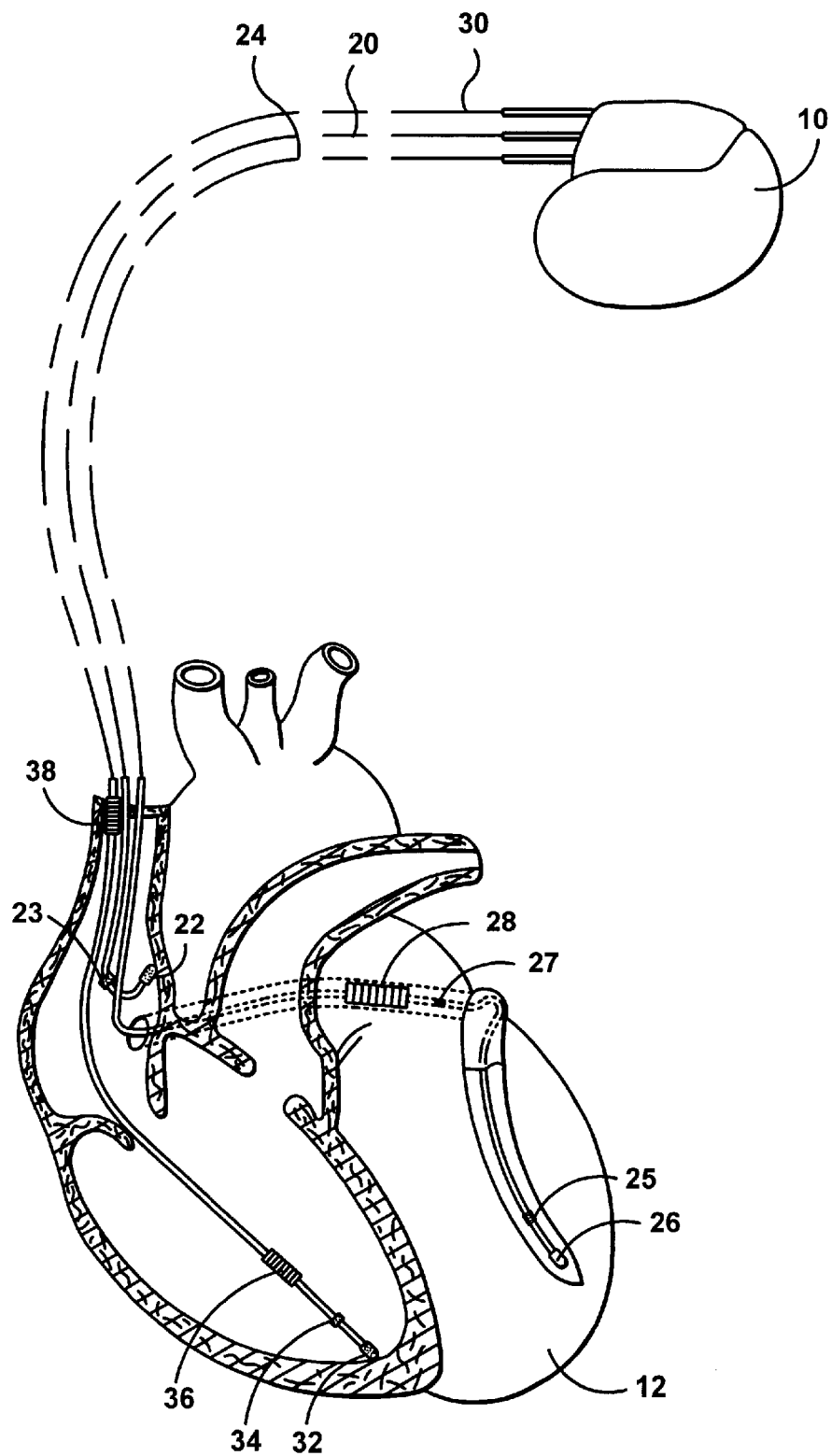
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22 and an atrial ring electrode 23, which typically is implanted in the patient's right atrial appendage.

To sense left atrial and ventricular cardiac signals and to provide left-chamber stimulation therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to sense atrial and ventricular cardiac signals and to deliver: left ventricular stimulation therapy using at least a left ventricular tip electrode 26, left atrial stimulation therapy using at least a left atrial ring electrode 27, and shocking therapy using at least a left atrial coil electrode 28. In an alternative embodiment, the coronary sinus lead 24 may also include a left ventricular ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
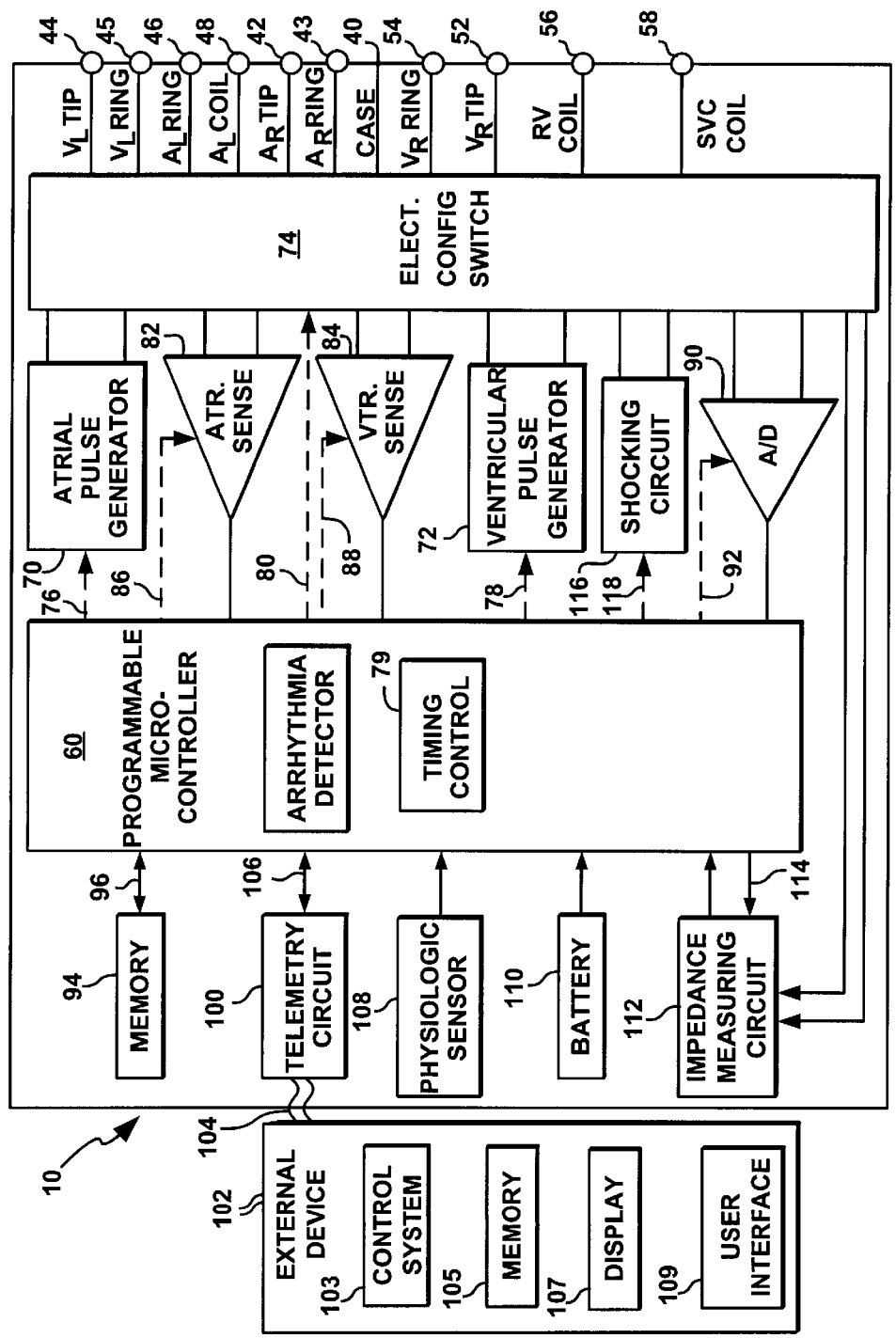
FIG. 2 is a functional block diagram of the multi-chamber implantable stimulation device of FIG. 1, illustrating the basic elements that provide cardioversion, defibrillation and pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber stimulation device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The stimulation device 10 further includes a connector having a plurality of terminals, 42, 43, 44, 45, 46, 48, 52, 54, 56, and 58 (shown schematically and, for convenience, the names of the electrodes to which they are connected are shown next to the terminals). As such, to achieve right atrial sensing and stimulation, the connector includes at least a right atrial tip terminal 42 adapted for connection to the atrial ($A_R$) tip electrode 22. The connector may also include a right atrial ring terminal ($A_R$ RING) 43 for connection to the atrial ring electrode 23.

To achieve left chamber sensing and stimulation, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial tip electrode 27, and the left atrial coil electrode 28, respectively.

To support right chamber sensing and stimulation, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

As shown in FIG. 2, an atrial pulse generator 70 and a ventricular pulse generator 72 generate stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, cross chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity. For example, during the operation of the automatic capture calibration procedure in accordance with present invention, stimulation of the right ventricle or the left ventricle may be in a unipolar or bipolar mode, while sensing is in a unipolar mode.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. In accordance with the present invention, the gain of the atrial sensing circuit or the ventricular sensing circuit 84 can be automatically adjusted under the control of the external programmer 102 in order to meet the requirements needed to perform the automatic capture calibration procedure.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external programmer 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". The microcontroller 60 detects a depolarization signal during a window following a stimulation pulse. The microcontroller 60 enables capture detection by triggering the ventricular pulse generator 72 to generate a stimulation pulse, starting a stimulation response window using the timing circuitry within the microcontroller 60, and enabling the data acquisition system 90 via control signal 92 to sample the cardiac signal that falls in the capture detection window and, based on a capture detection threshold parameter of the sampled cardiac signal, determines if capture has occurred. As it will be described herein, the present invention includes a calibration procedure for determining whether or not it is recommended to enable automatic capture in a particular patient, and, if so, it further determines the capture detection threshold based on the integration of the sampled depolarization signal during a stimulation response window.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external programmer 102. The telemetry circuit 100 is activated by the microcontroller 60 by a control signal 106. The telemetry circuit 100 allows intracardiac electrograms and status information relating to the operation of the stimulation device 10 (as contained in the microcontroller 60 or memory 94) to be sent to the external programmer 102 through the established communication link 104.

The external programmer 102 includes a control system 103. Like the microcontroller 60 of device 10, control system 103 typically includes a microprocessor, or equivalent control circuitry, designed for controlling the delivery of stimulation therapy, and may further include RAM or ROM memory, logic and timing circuitry, state machine circuitry, and I/O circuitry. Typically, the control system 103 includes the ability to process or monitor input signals (data) as controlled by a program code stored in a designated block of memory.

External programmer 102 further includes memory 105 in which operating parameters, input data associated with sampled cardiac signals received across communication link 104, or results of program operations carried out by control system 103 may be stored. In accordance with the present invention, control system 103 will execute a program code for performing an automatic capture calibration procedure using a paced depolarization integral method. Integration results as well as results from the statistical and mathematical analysis of these integration results produced during the execution of this calibration procedure will be stored in memory 105.

External programmer 102 also includes a display 107 which may be an LCD screen or a similar monitor. Messages related to the programming of the device 10 can be communicated to a medical practitioner on display 107. For example, recommendations for or against enabling the automatic capture feature of device 10, automatic capture calibration variable estimations, or calibration procedure failure conditions can be displayed during the operation of the automatic capture calibration procedure of the present invention.

External programmer 102 also includes a user-interface 109 which may be a keyboard, a mouse, or any other similar device that allows the medical practitioner to make selections or issue commands relating to the operating parameters of device 10 as well as the operation parameters of the control system 103 of the external programmer 102. For example, the automatic capture calibration procedure included in the present invention is initiated by control system 103 upon receiving a command from the user interface 109.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V—V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected. The stimulation device 10 further includes a magnet detection circuitry coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 by a control signal 114.

It is a function of the stimulation device 10 to operate as an implantable cardioverter/defibrillator (ICD) device, and thus it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 to 40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
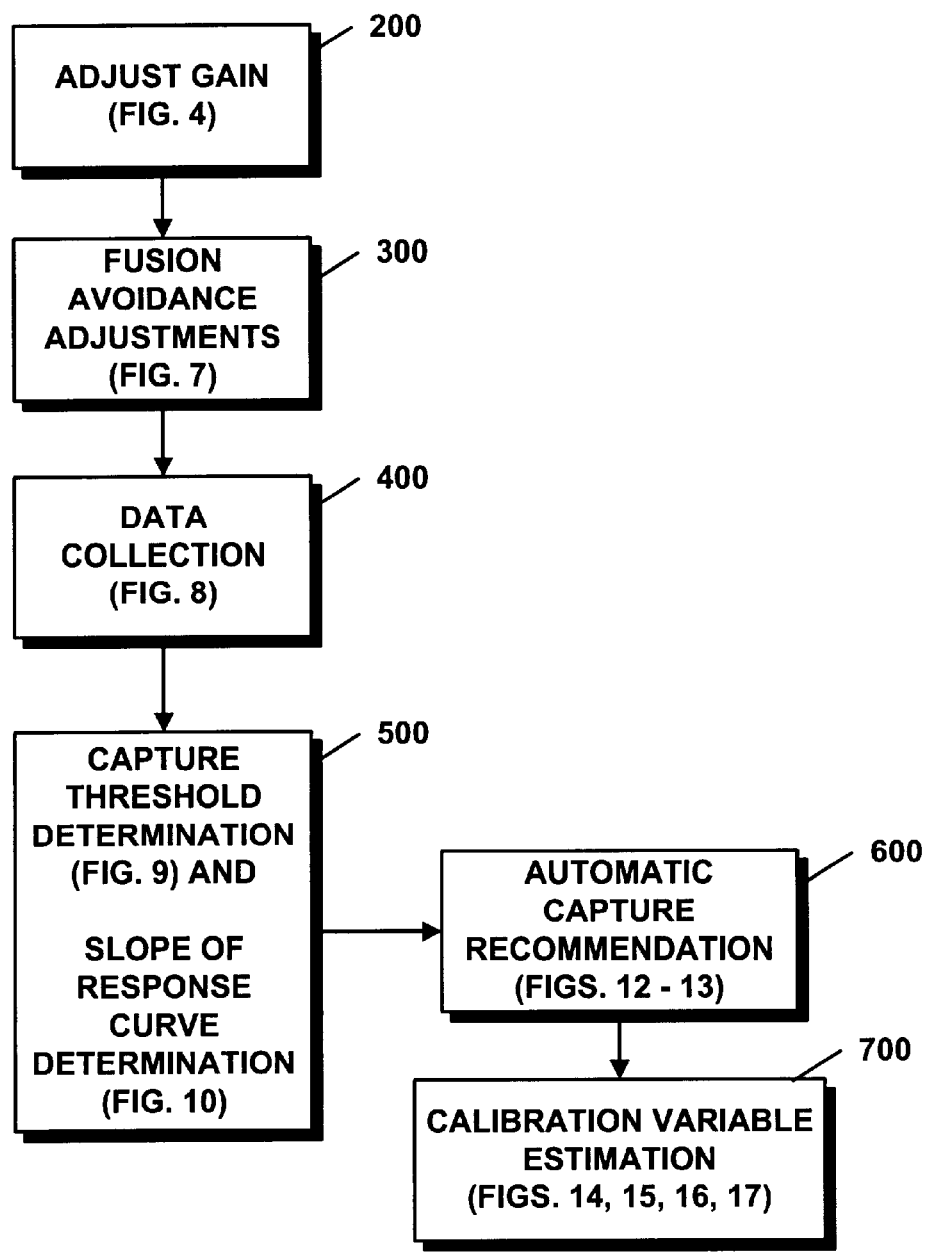
FIG. 3 is a flow chart describing an overview of the operation of one embodiment of the present invention for performing an automatic automatic capture calibration procedure using a paced depolarization integral method.

In FIG. 3, a flow chart is shown describing an overview of the operation and features of a pacing (or stimulation) depolarization integral (PDI) calibration process 150 implemented in one embodiment of the cardiac stimulation system of FIG. 2. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The control program for executing the calibration process 150 is stored in the memory of control system 105 of external programmer 102 (FIG. 2). A medical practitioner using the user-interface 109 can initiate the calibration process 150 by selecting a "Unipolar PDI-Method Calibration" command. Upon receiving this calibration command, a number of parameters are automatically programmed by external programmer 102 into the implanted device 10 via communication link 104 (FIG. 2). These parameters are shown in Table I below with the preferred initial settings that are automatically programmed in the stimulation device 10. The calibration process 150 will be described as applied in a ventricular chamber, it being understood that the calibration process 150 could be modified for application in an atrial chamber. It should be understood, however, that a different set of initial settings pertaining to atrial automatic capture shall be automatically programmed.

TABLE I

Initial settings

| Parameter | Preferred Setting |
|---|---|
| Recharge | 16.05 msec |
| Block Overlap | 0.98 msec |
| A/D Converter Offset | 0 |
| Ventricular EGM Gain | 50 |

TABLE I-continued

Initial settings

| Parameter | Preferred Setting |
|---|---|
| AV/PV Delay | 50/25 msec |
| Back-up Pulse delay | 100 msec |
| Back-up Pulse amplitude | 4.5 V |
| Primary Pulse amplitude | 4.5 V |
| Response Window | 66 msec |
| Automatic Capture Mode | Calibrate |

After the automatic programming of the parameters in Table I, the external programmer 102 initiates the calibration process 150 (FIG. 3). The calibration process 150 calls upon a series of subroutines (or processes) 200, 300, 400, 500, 600, and 700. Throughout the calibration process 150, certain failure conditions may cause the calibration procedure to be aborted. These failure conditions are listed in the following Table II and will be further described below.

TABLE II

Failure Test Conditions

| # | FAILURE CONDITION | DISPLAY |
|---|---|---|
| 1 | Ventricular EGM gain setting of 5 reached with signal samples < pre-defined maximum magnitude (Decision step 220, subroutine 200, FIG. 4) | "Insufficient evoked response detected and/or lead polarization is too large. Test cannot be run." |
| 2 | Coefficient of Variation or standard deviation of average PDI at 4.5 Volts exceeds upper limit (Decision steps 320 and 330, subroutine 300, FIG. 7) | "Test cannot be run due to insufficient paced activity. Possible fusion beats or extreme variability in measurements." |
| 3 | Average PDI at 4.5 Volts is less than a minimum acceptable value (Decision step 505, subroutine 500, FIG. 9) | "Test cannot be run due to inappropriate threshold found. automatic capture cannot be enabled." |
| 4 | PDI at 0 Volt exceeds a maximum acceptable value (Decision step 510, subroutine 500, FIG. 9) | "Test cannot be run due to inappropriate threshold found. Automatic capture cannot be enabled." |
| 5 | Capture threshold = 4.5 Volts (Decision step 560, subroutine 500, FIG. 10) | "Test cannot be run due to inappropriate threshold found. Automatic capture cannot be enabled." |
| 6 | No ▫PDI above temporary detection threshold (step 536, FIG. 9) | "Test cannot be run due to inappropriate threshold found. Automatic capture cannot be enabled." |

The calibration process 150 starts with subroutine 200 that automatically adjusts the gain applied to the ventricular EGM signal by ventricular sensing circuit 84 as will be described in detail in conjunction with FIG. 4. Next, a subroutine 300 is called upon by the calibration process 150 for determining whether fusion activity is suspected. If so, a message is displayed on display 107 (FIG. 2) recommending an adjustment to the pacer timing parameters that will minimize the likelihood of fusion. The methods of subroutine 300 for fusion avoidance will be described in greater detail in conjunction with FIG. 7.

Next, subroutine 400 is called upon to collect paced depolarization integral data following a range of stimulation pulse energies, such that the capture threshold pulse energy, the capture detection threshold to be used during automatic capture, as well as other parameters used during automatic capture operations may be determined. The data collection techniques of subroutine 400 will be described in greater detail in conjunction with FIG. 8.

Briefly, during subroutine 400, the ventricular EGM signal received by ventricular sensing circuit 84 is sampled following the delivery of a series of stimulation pulses of varying pulse amplitudes. The sampled signals are integrated over a pre-defined response time window following each stimulation pulse to obtain a paced depolarization integral or "PDI" associated with each stimulation pulse amplitude. In this way, evoked response signal data and polarization signal data is collected and stored.

Figure 9:
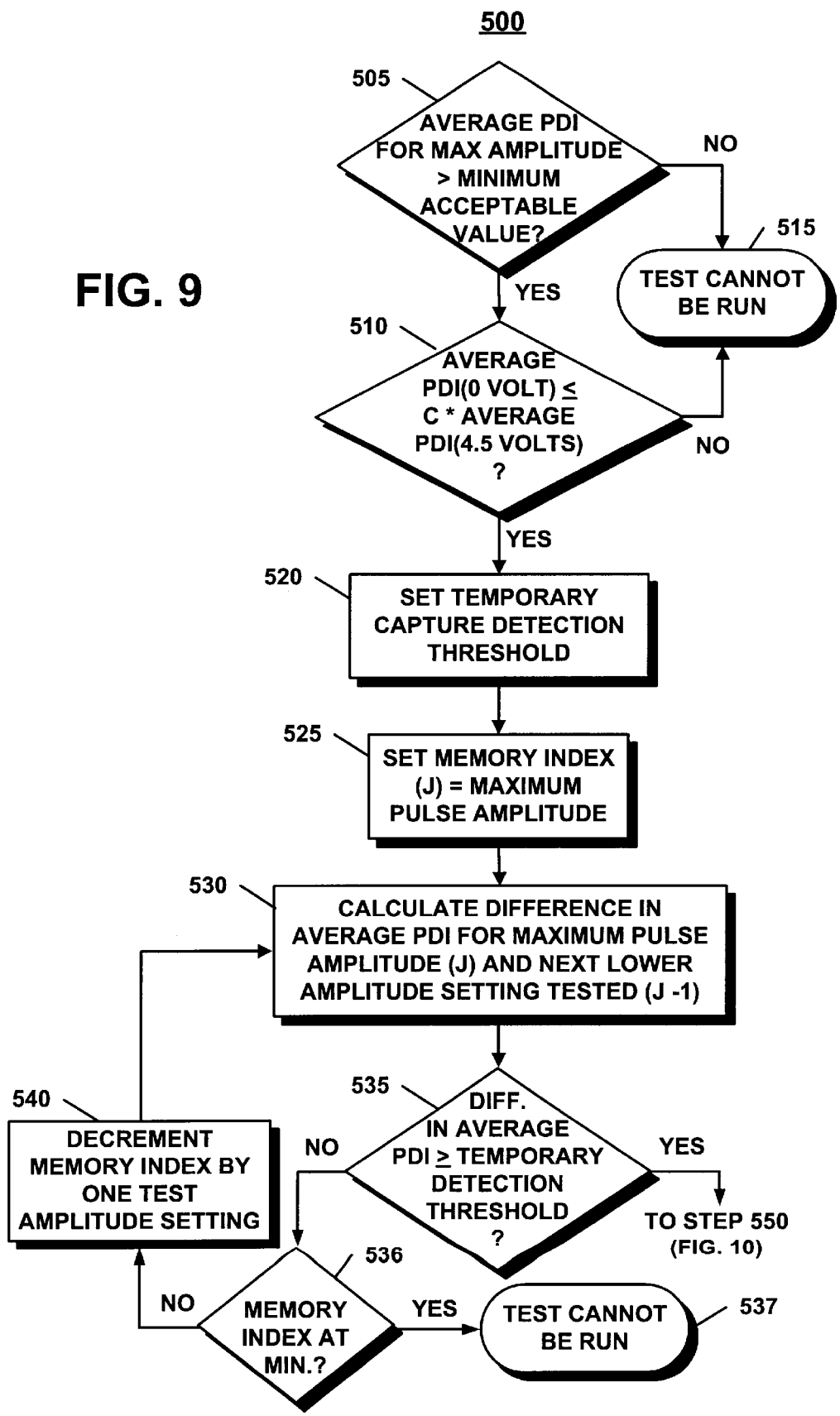
FIGS. 9 and 10 illustrate a flow chart describing a method used in the operation of FIG. 3 for determining the capture threshold, slope, and intercept of a response curve.

Next, calibration process 150 calls upon subroutine 500 which, using the data collected during subroutine 400, determines the capture threshold, as it will be further described in conjunction with FIG. 9. The data collected in method 400 is further used by subroutine 500 to determine the slope of the stimulation response curve (e.g. the stimulation pulse amplitude versus the paced depolarization integral) as will be described in conjunction with FIG. 10.

Next, subroutine 600 performs a mathematical analysis of the data collected during subroutine 400 to determine whether automatic capture can be performed successfully during unipolar sensing. This analysis is described in greater detail in conjunction with FIGS. 11 and 12.

Subroutine 700 then displays a message recommending or not recommending automatic capture based on the results of subroutine 600. Whether automatic capture is recommended or not, subroutine 700 calculates estimations of pertinent calibration variables related to the evoked response signal data and the polarization signal data and reports these variables on display 107, as it will be described in conjunction with FIGS. 14, 15, 16, and 17.

The medical practitioner, having the automatic capture recommendation made by subroutine 600, and the calibration variable estimation report made by subroutine 700, can now make informed decisions in enabling automatic capture and selecting related parameters to be used by the stimulation device 10 during automatic capture execution.

Figure 4:
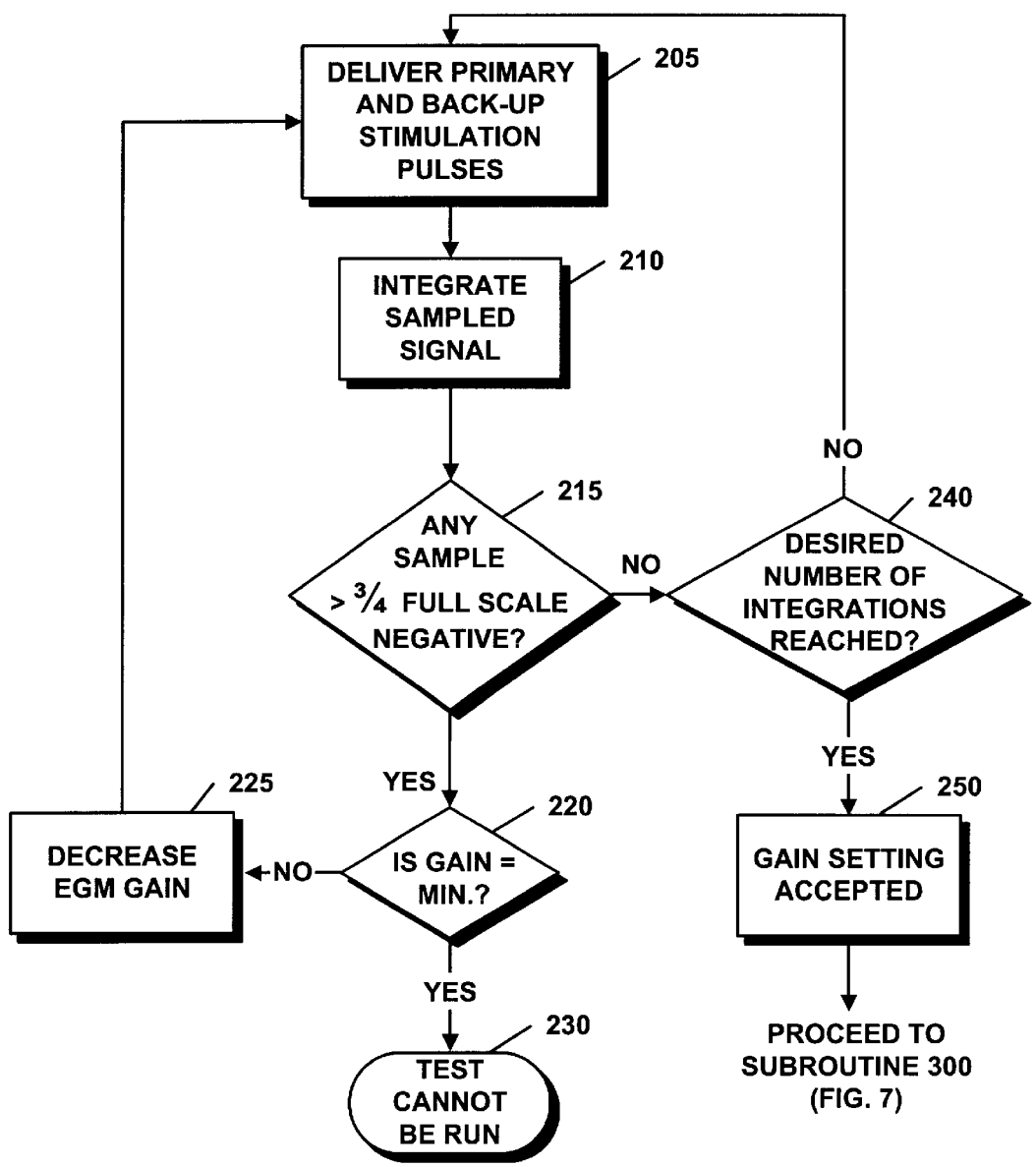
FIG. 4 is a flow chart describing a method used in the operation of FIG. 3 for automatically adjusting the gain of sensing circuits of the stimulation device of FIG. 2.

The flow chart of FIG. 4 depicts one embodiment of the subroutine 200 called upon by calibration process 150 to automatically adjust the gain of ventricular sensing circuits 84 (FIG. 2). The external programmer 102 triggers the stimulation device 10 to deliver a pair of stimulation pulses at step 205. The first pulse is the primary stimulation (or pacing) pulse and has an amplitude equal to the initial setting, preferably 4.5 V (Table I), which is automatically programmed by the external programmer 102 upon receiving the command to perform the calibration process 150. The pulse width is a pre-defined value, preferably 0.4 msec (Table I). The primary stimulation pulse is followed by a back-up stimulation pulse delivered after a given time delay, preferably 100 msec (Table I), following the delivery of the primary stimulation pulse. The pulse amplitude of the back-up pulse is set to a maximum setting, preferably 4.5 V (Table I).

The electrogram (EGM) signal received by the ventricular sensing circuit 84 and sampled by the A/D converter 90 is transmitted via the communication link 104 to the external programmer 102. The sampling frequency is preferably 256 samples per second. The sampled signal is integrated at step 210 of subroutine 200. This integration is performed over a pre-defined response window, preferably 66 msec in duration (Table I) starting at a given offset, preferably 17 msec, following the delivery of the primary stimulation pulse. An integration baseline, or zero-level, is determined by averaging the magnitude of specified signal samples, preferably the second and third samples occurring during the post-pulse fast recharge period. Only negative signal samples, that is samples that are less than the integration baseline, are integrated at step 210.

Figure 5:
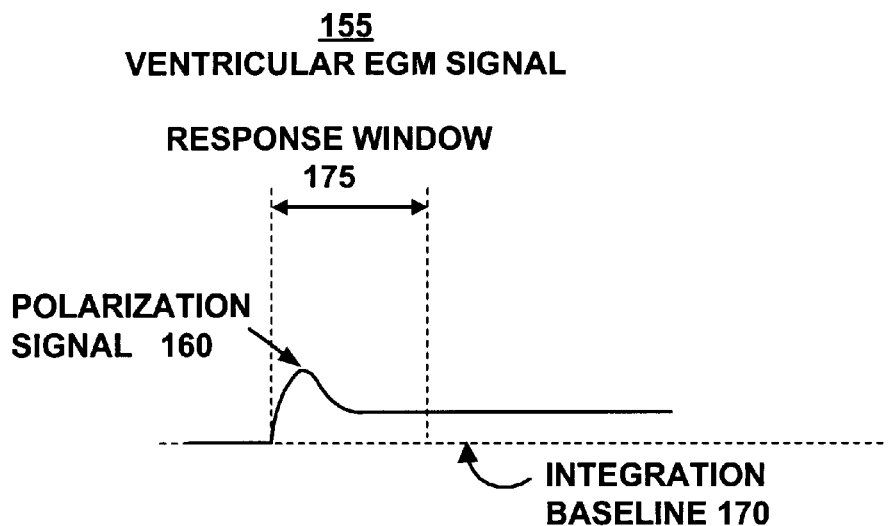
FIG. 5 depicts a ventricular electrogram signal immediately following the delivery of a stimulation pulse which is less than a capture threshold.
Figure 6:
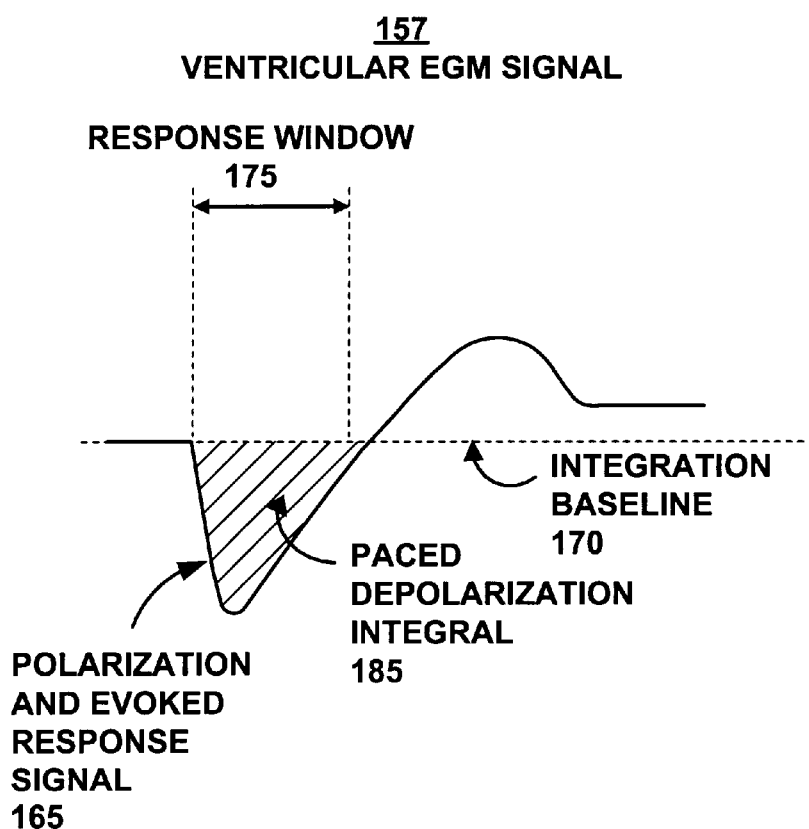
FIG. 6 depicts a ventricular electrogram signal immediately following delivery of a stimulation pulse which is equal to, or greater than the capture threshold.

Referring now to FIGS. 5 and 6, they illustrate the integration step 210 described above. Two sample ventricular EGM signals 155 (FIG. 5) and 157 (FIG. 6) are shown. The EGM signal 155 represents a post-stimulation signal occurring when the stimulation pulse amplitude is at a low level, less than the capture threshold. The EGM signal 155 includes only the lead polarization signal 160 but not an evoked response signal, and is sampled during a response window 175. Sample points, indicated by heavy dots on the chart, that occur below an integration baseline 170, are summed to obtain the paced depolarization integral 180 associated with the lead polarization signal due to a sub-threshold pulse amplitude.

The EGM signal 157 represents a post-stimulation signal that occurs when the stimulation pulse amplitude is above the capture threshold, as would be the case during the operation of subroutine 200 (FIG. 4). The EGM signal 157 includes both the lead polarization signal 160 and an evoked response signal 165. All sample points occurring during the response window 175 that are below the integration baseline 170 are summed to obtain the paced depolarization integral 185 associated with both the effects of lead polarization and the evoked response due to stimulation at or above the capture threshold.

The response signals during both supra-threshold (captured) stimulation beats and sub-threshold (non-captured) stimulation beats are thus characterized. Measuring the response signal during non-captured beats allows the lead polarization signal to be characterized. Measuring the response signal during captured beats allows the evoked response signal to be characterized. It is the difference in these signals that will determine whether automatic capture can be recommended as will be further described later in conjunction with FIGS. 12 and 13.

Referring back to FIG. 4, at decision step 215, the absolute magnitude of all signal samples included in the integration are compared to a maximum magnitude. If any sample is less than a pre-defined maximum magnitude, preferably % of the full scale negative, the integration is not accepted, and subroutine 200 proceeds to decision step 220. At decision step 220, the subroutine 200 determines if the gain applied to the EGM signal by ventricular sensing circuit 84 is equal to a pre-defined minimum gain, preferably 5. If the gain is not equal to the minimum gain allowed, the gain is decreased by one setting at step 225, and subroutine 200 returns to step 205 to collect the EGM signal following the next primary stimulation pulse at the new gain setting.

If, at decision step 220, it is determined that the gain reaches the minimum acceptable setting, and the absolute magnitude of any of the signal samples is less than the required maximum magnitude, subroutine (or method 200) is terminated at step 230 and a message is displayed on display 107 (FIG. 1), alerting the medical practitioner that the calibration process 150 cannot be performed. In this case, the evoked response is insufficiently detected and/or the lead polarization signal is too large precluding the integration process from yielding the necessary data for automatic capture calibration at any available gain setting. A message to this extent is displayed on external programmer 102 (see failure condition 1 depicted in Table II below).

If all signal samples meet the magnitude requirement at decision step 215 of FIG. 4, then subroutine 200 determines at decision step 240 if the desired number of integrations have been performed. Preferably, a sequence of four primary and back-up simulation pulse pairs is delivered, such that four integrations over the response window following the primary stimulation pulse are performed. Subroutine 200 returns to step 205 until the desired number of integrations have been performed. Having performed the desired number of integrations with all sample points meeting the magnitude criteria of decision step 215, the gain setting is considered acceptable at step 250, and the calibration process 150 proceeds to the fusion avoidance subroutine 300 of FIG. 7.

Figure 7:
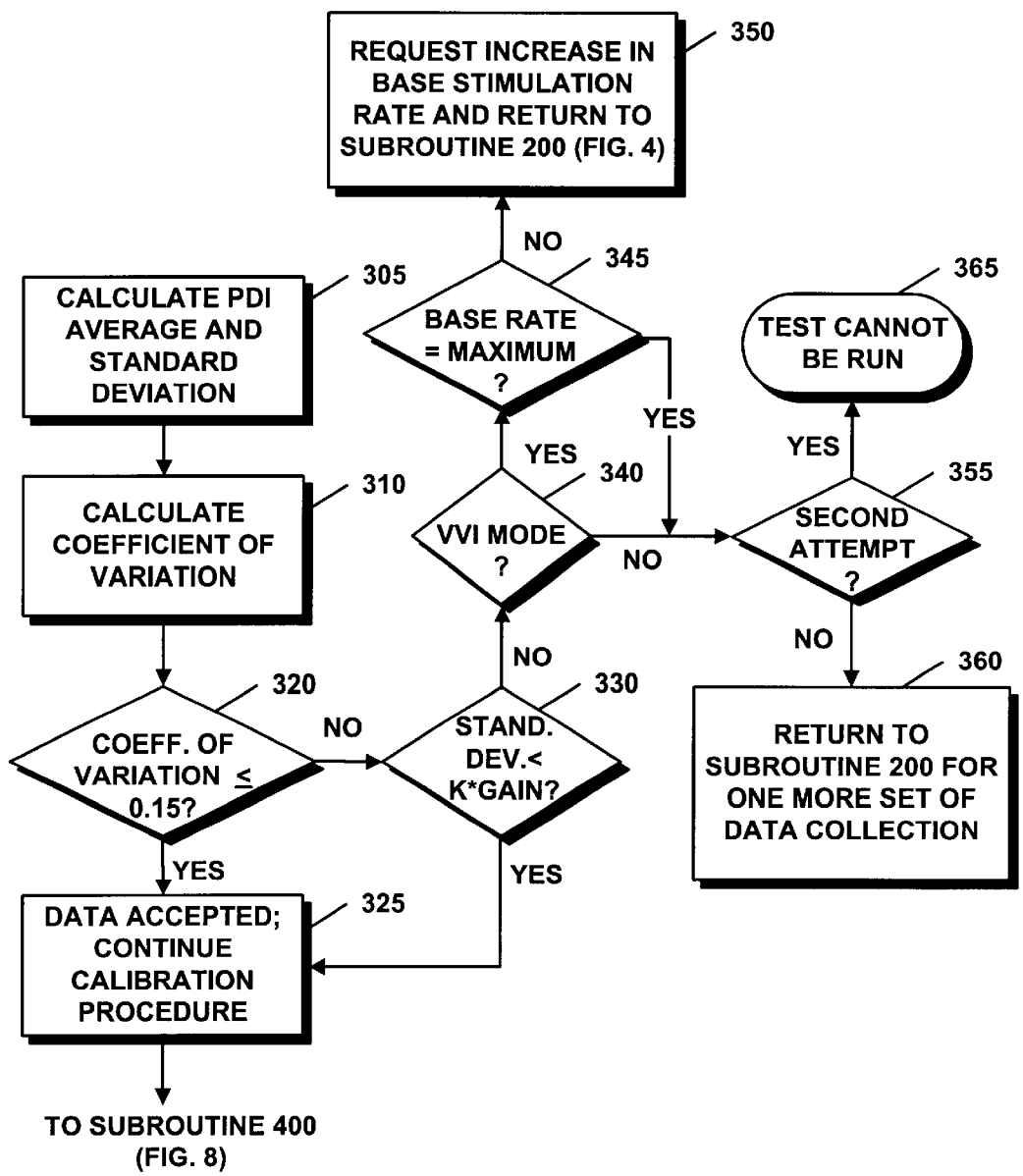
FIG. 7 is a flow chart describing a method used in the operation of FIG. 3 for automatically adjusting stimulation parameters in order to avoid fusion.

In FIG. 7, a process flow chart is shown depicting the details of one embodiment of the fusion avoidance subroutine 300 called upon by calibration process 150 of FIG. 3 to determine if fusion activity is suspected. To this end, the variability of the paced depolarization integrals determined during subroutine 200 is assessed. Beginning at step 305, the paced depolarization integrals (PDI) determined from the last set of stimulation pulses delivered during subroutine 200 are averaged. The standard deviation (SD) of these paced depolarization integrals is also calculated at step 305. This average paced depolarization integral corresponds to the ventricular EGM signal in response to a maximum pulse amplitude, in the present example 4.5 Volts, amplified by the final accepted gain setting determined in subroutine 200.

At step 310, the coefficient of variation (CV) of this average paced depolarization integral is calculated by dividing the standard deviation (SD) calculated by the average calculated in step 305, as represented by the following equation:

$$CV=SD/\text{AVERAGE}$$

At step 320, this coefficient of variation (CV) is compared to a predefined maximum value, preferably 0.15. If the coefficient of variation is less than this predefined maximum value, then the paced depolarization integral data is considered acceptable at step 325, and the calibration process 150 continues by proceeding to subroutine 400 of FIG. 8 to be described later.

If, however, subroutine 300 determines at step 320 that the coefficient of variation is greater than the maximum value, the standard deviation (SD) of the paced depolarization integral is compared at step 330 to a multiple, K, of the gain setting applied to the EGM signal by the ventricular sensing circuit 84. Preferably, K is set equal to 3. If the standard deviation is less than 3 times the gain setting, then the paced depolarization integral data is still considered acceptable at step 325, and the calibration process 150 continues by proceeding to subroutine 400 of FIG. 8.

If, however, subroutine 300 determines at step 330 that the standard deviation is not less than 3 times the gain setting, that is the variability criteria at decision steps 320 and 330 are not met, fusion activity is suspected due to large variation in the data. If the stimulation device 10 is in WI mode, as determined at decision step 340, and the base stimulation rate is not already at the maximum setting as determined at decision step 345, the external programmer 102 displays a message at step 350 indicating that insufficient stimulation activity has occurred and that the base stimulation rate is increased in order to reduce the likelihood of fusion. Subroutines 200 (FIG. 4) and 300 will then be repeated until the variability criteria of steps 320 and 330 are met.

If the maximum base rate has been reached as determined at decision step 345, or if the stimulation device 10 is in DDD mode rather than WI mode as determined at decision step 340, the external programmer 102 will attempt once more to collect acceptable data by returning to subroutine 200 at step 360.

If, however, the variability criteria are still not met after the second attempt (decision step 355), the calibration process 150 is terminated at step 365, and external programmer 102 displays a message indicating that the test cannot be performed because of insufficient paced activity due to possible fusion beats or because of extreme variability in the measurements (see failure condition 2 in Table II below).

Figure 8:
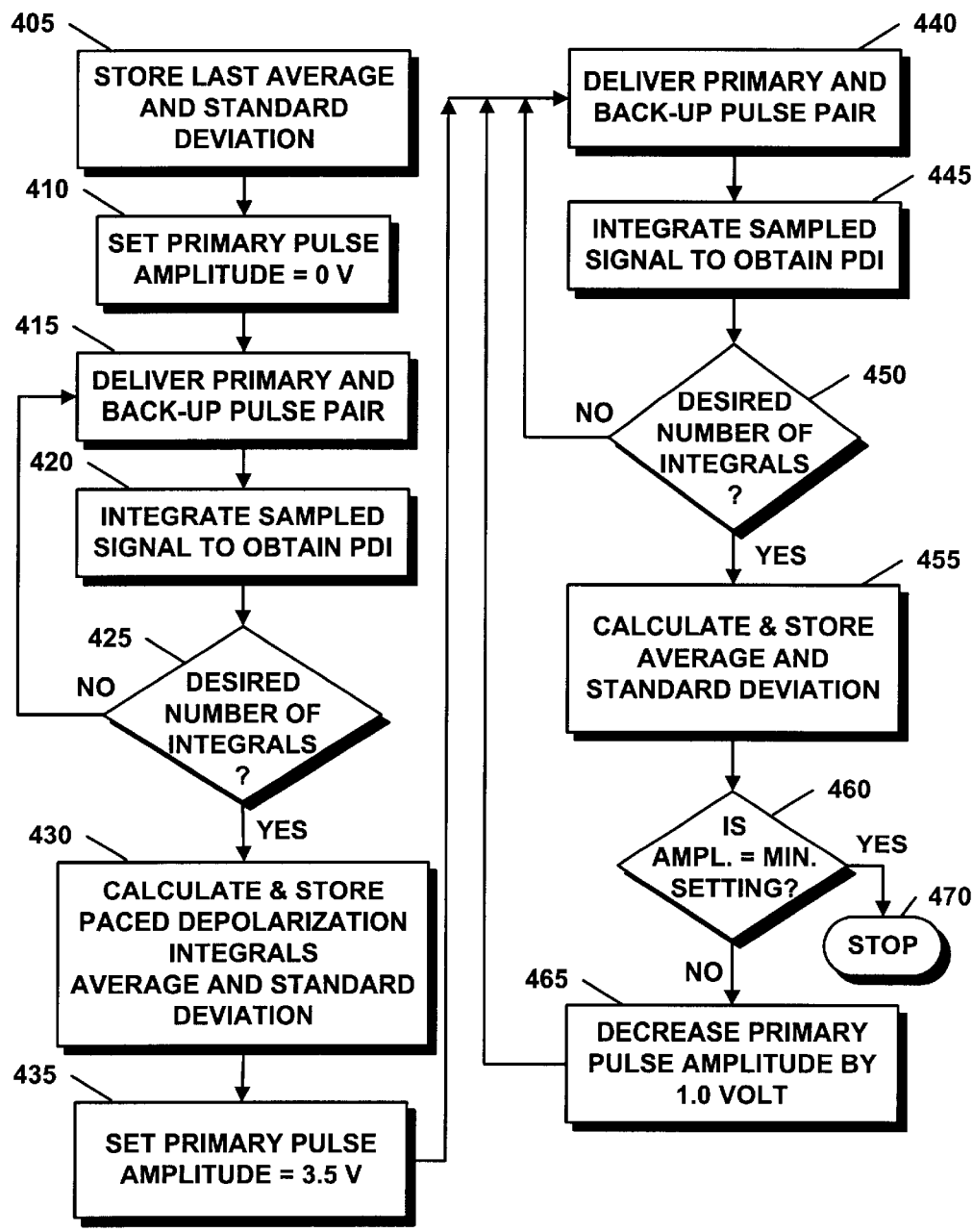
FIG. 8 is a flow chart describing a method used in the operation of FIG. 3 for collecting paced depolarization integral data related to an evoked response signal and the polarization signal following the delivery of an electrical stimulation pulse.

Turning now to FIG. 8, it illustrates a process flow chart that depicts the details of one embodiment of the subroutine 400 called upon by the calibration process 150 for collecting and storing paced depolarization integral data. Essentially, the external programmer 102 triggers the stimulation device 10 to deliver a given number of primary and back-up stimulation pulse pairs, preferably four at each pacing voltage (4.5V, 3.5V, 2.5V, 1.5V, 0.5V, 0V). The stimulation pulses are delivered over a range of pulse amplitudes including both supra-capture threshold amplitudes and sub-capture threshold amplitudes. The back-up stimulation pulse is delivered at a maximum amplitude, preferably 4.5 Volts to maintain a desired heart rate throughout the test.

After each primary stimulation pulse, the external programmer 102 determines the paced depolarization integral by integrating the sampled ventricular signal during the response window in the same manner described earlier in conjunction with FIGS. 5 and 6. Hence, the average paced depolarization integral and its standard deviation can be calculated for each tested pulse amplitude setting. The average paced depolarization integral for each pulse amplitude setting and the associated standard deviation are then stored in memory 105 (FIG. 2) with a pulse amplitude index.

Data collection subroutine 400 of FIG. 8 begins at step 405 by storing the average and standard deviation of the last set of paced depolarization integrals used in the automatic gain adjustment subroutine 200 of FIG. 4 and the fusion avoidance subroutine 300 of FIG. 7. These values are associated with the maximal stimulation pulse amplitude, preferably 4.5 V, and are stored in memory 105 of FIG. 2, with the index indicating the stimulation pulse amplitude.

At step 410, the pulse amplitude for the primary stimulation pulse is adjusted to 0 V. At step 415, a primary and back-up stimulation pulse pair is delivered. At step 420, the ventricular EGM signal sensed by ventricular sensing circuit 84 and digitized and sampled by the A/D converter 90 of FIG. 2, is integrated by the external programmer 102, in order to obtain the paced depolarization integral (PDI) associated with a stimulus of 0 Volt. As described previously, the integration is performed only on samples more negative than the integration base line and occurring within the response window following the primary stimulation pulse.

At decision step 425, subroutine 400 determines if the desired number of integrals, preferably four, have been obtained at the existing primary pulse amplitude setting. If not, subroutine 400 returns to step 415 to deliver another primary and back-up pulse pair at the same primary pulse amplitude setting.

Once the desired number of paced depolarization integrals have been obtained, as determined at decision step 425, the average paced depolarization integral and its standard deviation for the existing primary pulse amplitude, 0 Volt, are calculated and stored in memory 105 with an index indicating the pulse amplitude.

At step 435, the primary pulse amplitude is adjusted to a setting one increment below the maximal setting. In the present example, an increment of 1.0 Volt is preferred, therefore the primary pulse amplitude is set to 1.0 Volt less than the maximal 4.5 Volt setting, i.e. at 3.5 Volts.

Subroutine 400 then performs the same operations of delivering a primary and back-up stimulation pulse pair at step 440, integrating the ventricular signal to obtain the paced depolarization integral (PDI) at step 445 obtained for a given number of stimulated beats (decision step 450), so that an average paced depolarization integral (PDI) and its standard deviation (SD) can be calculated and stored in memory 105 with a pulse amplitude index (step 455).

Subroutine 400 will then decrement the primary pulse amplitude at step 465, in this example by 1.0 Volt, after first verifying, at decision step 460, that the existing pulse amplitude is not already at the lowest setting to be tested above the minimal 0 Volt setting, preferably 0.5 Volts. Thus, in this example, the paced depolarization integrals will be collected following stimulation pulse amplitudes of 3.5 Volts, 2.5 Volts, 1.5 Volts and 0.5 Volt, in addition to the maximal and minimal amplitudes of 4.5 Volts and 0 Volt.

If the pulse amplitude is not already at 0.5 Volt as determined at decision step 460, the primary pulse amplitude is decreased by 1.0 Volt at step 465, and steps 440 through 460 are repeated to obtain the average paced depolarization integral (PDI) and its standard deviation for each test amplitude setting. Subroutine 400 has then completed the paced depolarization integral data collection and storage operations and is terminated at step 470. The calibration process 150 then proceeds to the capture threshold determination subroutine 500 of FIGS. 9 and 10.

Figure 10:
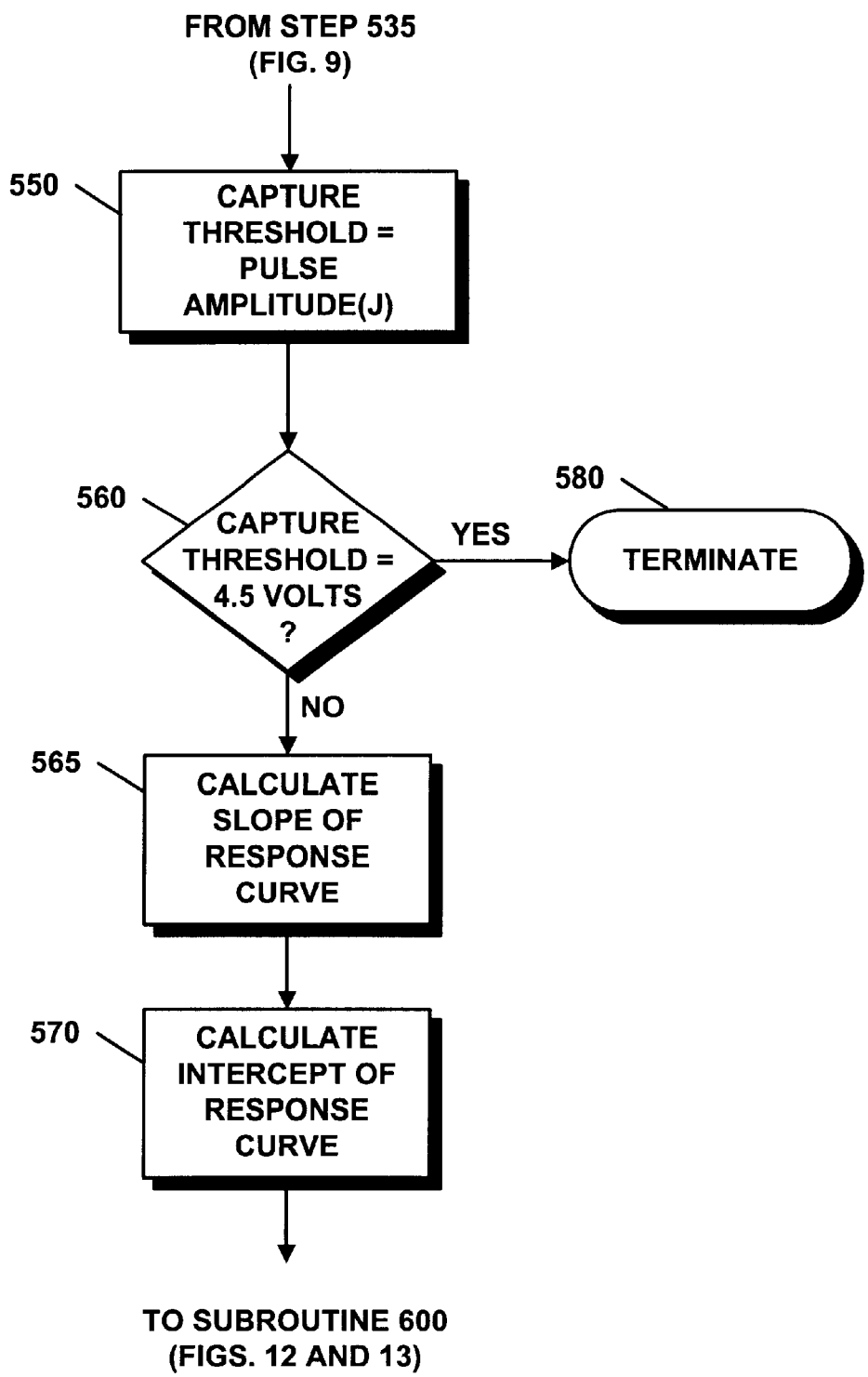

In FIGS. 9 and 10, a flow chart is shown depicting the details of one embodiment of the capture threshold determination subroutine 500 called upon by the calibration process 150 for evaluating the paced depolarization integral data collected during the data collection subroutine 400 of FIG. 8. FIG. 9 illustrates the method of determining capture threshold, and FIG. 10 illustrates the method of determining the slope of the stimulation response curve.

Subroutine 500 begins at decision step 505 by comparing the average paced depolarization integral (PDI) obtained for the maximum pulse amplitude tested, in this example 4.5 Volts. The lowest average paced depolarization integral for all supra-threshold pulse amplitudes is expected to occur at the maximum pulse amplitude, because lead polarization is usually positive and increases with the stimulation voltage. If the lowest average paced depolarization integral is less than the minimum acceptable value, for example a value of 180, then the calibration process 150 of FIG. 3 cannot be performed because the evoked response signal is insufficient, and the calibration process 150 is terminated at step 515. The external programmer 102 displays a message indicating insufficient evoked response amplitude (refer to failure condition 3 in Table II below).

At step 510, the average paced depolarization integral for the minimum pulse amplitude tested, 0 Volt, is compared to a maximum acceptable value, preferably a multiple of the average paced depolarization integral for the maximum pulse amplitude, 4.5 Volts, such as 0.56 times the average paced depolarization integral for 4.5 Volts. If the average paced depolarization amplitude for 0 Volt exceeds the maximum acceptable value, an inappropriate capture detection at 0 Volt is indicated, causing the calibration process 150 to be aborted at step 515. At step 515, the external programmer 102 displays a message that the calibration process 150 cannot be performed, and further indicates that the automatic capture cannot be enabled due to an inappropriate threshold result (refer to failure condition 4 in Table II below).

If the criteria of steps 505 and 510 are met, subroutine 500 proceeds to step 520 and sets a temporary capture detection threshold. This temporary capture detection threshold represents the minimum difference that must exist between the paced depolarization integrals associated with two consecutive pulse amplitude settings in order to conclude that the higher of the two settings is the capture threshold. In other terms, the higher of the two pulse amplitude settings resulted in capture and the lower of the two pulse amplitude settings did not capture the heart. The temporary capture detection threshold is set according to the following equation:

$$TEMPDETTHR = MeanPDI(0.0V) + 0.5*(MeanPDI(4.5V) - MeanPDI(0.0V), \quad (1)$$

wherein:

TEMPDETTHR=the temporary capture detection threshold;

MeanPDI(0 Volt)=the average paced depolarization integral calculated in response to a primary stimulation pulse 0 Volt in amplitude; and MeanPDI(4.5 Volts)=the average paced depolarization integral calculated in response to a primary stimulation pulse 4.5 Volts in amplitude.

At step 525 of FIG. 9, a memory index, J, is set equal to the maximum pulse amplitude tested, 4.5 Volts in the present example. At step 530, the difference in the average paced depolarization integral ($\Box$PDI) for this maximum pulse amplitude and the next lower amplitude setting tested (J-1) is calculated, as shown in the following equation:

$$\Box PDI = PDI(J) - PDI(J-1).$$

In the present example, the average paced depolarization integral for 3.5 Volts is subtracted from the average paced depolarization integral for 4.5 volts. At decision step 535, this difference is compared to the temporary capture detection threshold set at step 520. If this difference is found to be greater than, or equal to the temporary capture detection threshold, then capture threshold has been found and is the pulse amplitude corresponding to the memory index J, in this case 4.5 V.

If the criteria at decision step 535 are not met, the memory index J is tested for a minimum at step 536, and, if it is not at a minimum, it is decremented at step 540 by one test amplitude setting so that the difference between the average paced depolarization integrals at the next two pulse amplitude settings can be compared at step 530, in this example, 3.5 Volts and 2.5 Volts. This process can be referred to as "step-down differencing." However, if at decision step 536 it is determined that the memory index J is at a minimum value, the calibration process 150 is terminated at step 537.

Steps 530, 535 and 540 are repeated until the difference between the two average paced depolarization integrals for two consecutive pulse amplitude settings is greater than, or equal to the temporary capture detection threshold. Thereupon, the capture threshold is stored in memory 105 as the pulse amplitude corresponding to memory index J at step 550 as shown in FIG. 10.

Subroutine 500 then continues to decision step 560 (FIG. 10), and, if it determines that the capture threshold is equal to the maximum pulse amplitude tested, in this example 4.5 Volts, then the slope of the response curve cannot be determined, and the calibration process 150 is terminated at step 580. External programmer 102 displays a message indicating that automatic capture cannot be enabled and that the calibration process 150 cannot be run due to an inappropriate threshold result (see failure condition 5 in TABLE II below).

If, however, it is determined at decision step 560 that the capture threshold is less than the maximum pulse amplitude tested, then subroutine 500 proceeds to determine the slope of the stimulation response curve at step 565, and its zero intercept at step 570, by performing a linear regression analysis on the paced depolarization integral data collected during the fusion avoidance subroutine 400 (FIG. 7).

The slope and intercept of the stimulation response curve are calculated according to the following equations:

$$\text{SLOPE} = \frac{N*\sum\{PA*MeanPDI(PA)\} - \{\sum PA\}*\{\sum MeanPDI(PA)\}}{N*\{\sum PA^2\} - \{\sum PA\}^2}$$

$$\text{INTERCEPT} = \frac{\{\sum MeanPDI(PA)\}*\{\sum PA^2\} - \{\sum PA\}*\{\sum PA*MeanPDI(PA)\}}{N*\{\sum PA^2\} - \{\sum PA\}^2}$$

wherein:
PA is the pulse amplitude;
MeanPDI(PA) is the average paced depolarization integral for a given pulse amplitude;
N is the number of pulse amplitude test settings occurring above the capture threshold setting.

The average paced depolarization integrals and pulse amplitude settings that are summed in the above equations only include those corresponding to amplitude settings greater than the capture threshold setting. An exception is made, however, if the capture threshold is found to be equal to the second highest amplitude setting tested, 3.5 Volts in the present example. In that case, the capture threshold amplitude setting and the highest amplitude setting are both used in the above equations such that at least two points are available to define the stimulation response curve.

Figure 11:
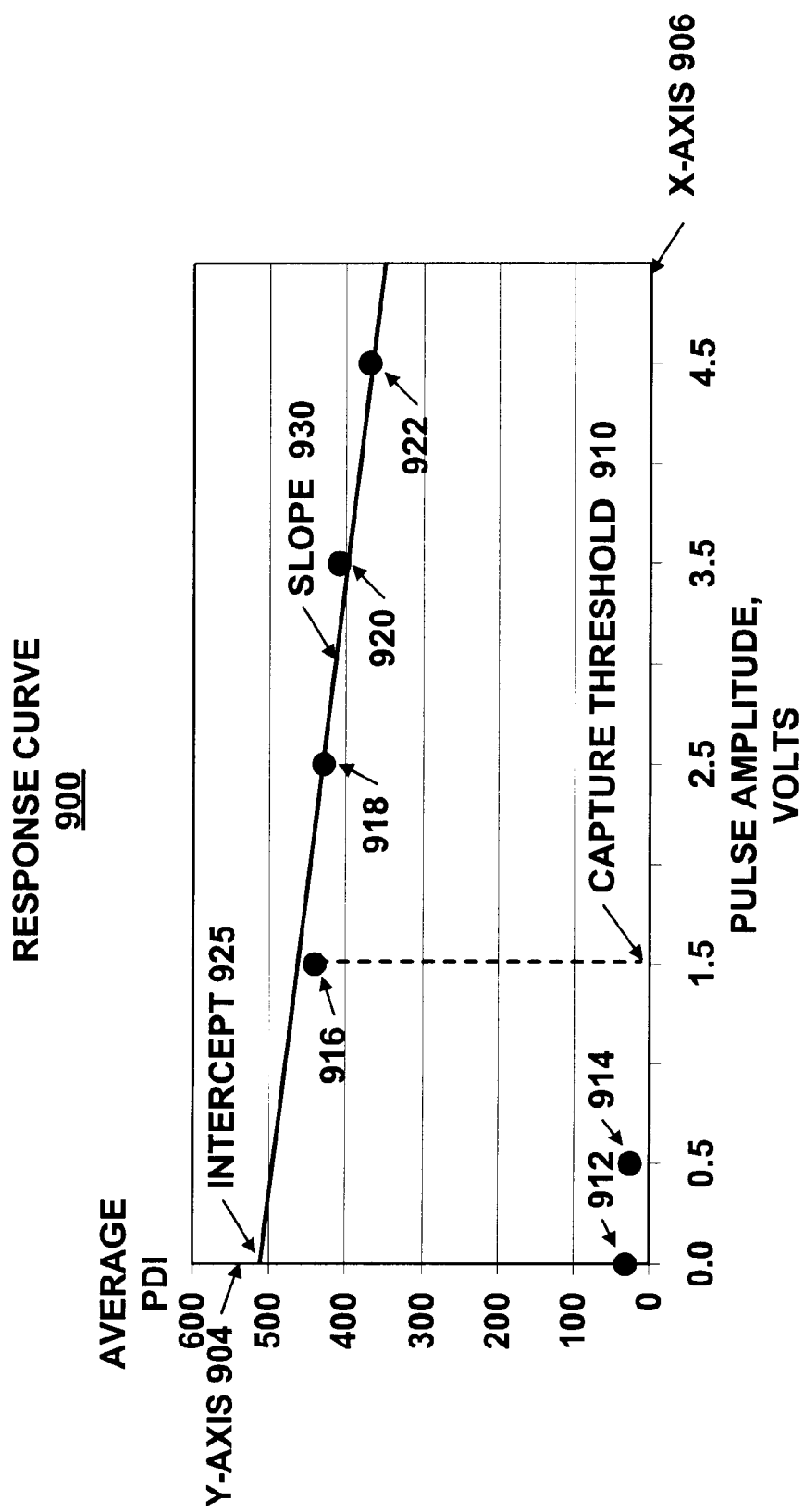
FIG. 11 is a graphical depiction of the stimulation-response curve obtained by collecting data according to the method of FIG. 8.

A plot of a sample stimulation response curve 900 is illustrated in FIG. 11. The average paced depolarization integral (PDI) is plotted along a Y-axis 904, and the tested stimulation pulse amplitudes are plotted along a X-axis 906. At stimulation pulse amplitudes of 0 Volt and 0.5 Volt, capture does not occur and the corresponding plotted points 912 and 914 have relatively low paced depolarization integral values. The plotted point 916 represents a considerably higher average paced depolarization integral and this point corresponds to the capture threshold 910 of 1.5 Volts.

All paced depolarization integrals for pulse amplitudes greater than 1.5 Volts, such as plotted points 918, 920, and 922 have relatively high average paced depolarization integral values. The linear regression analysis of subroutine 500 described above is applied to points 918, 920, and 922 with paced depolarization integral values corresponding to stimulation pulse amplitudes greater than the capture threshold. Thus, the slope 930 and the Y-intercept 925 are calculated in subroutine 500 (FIGS. 9 and 10) based on the line defined by these data points 918, 920, and 922.

Figure 12:
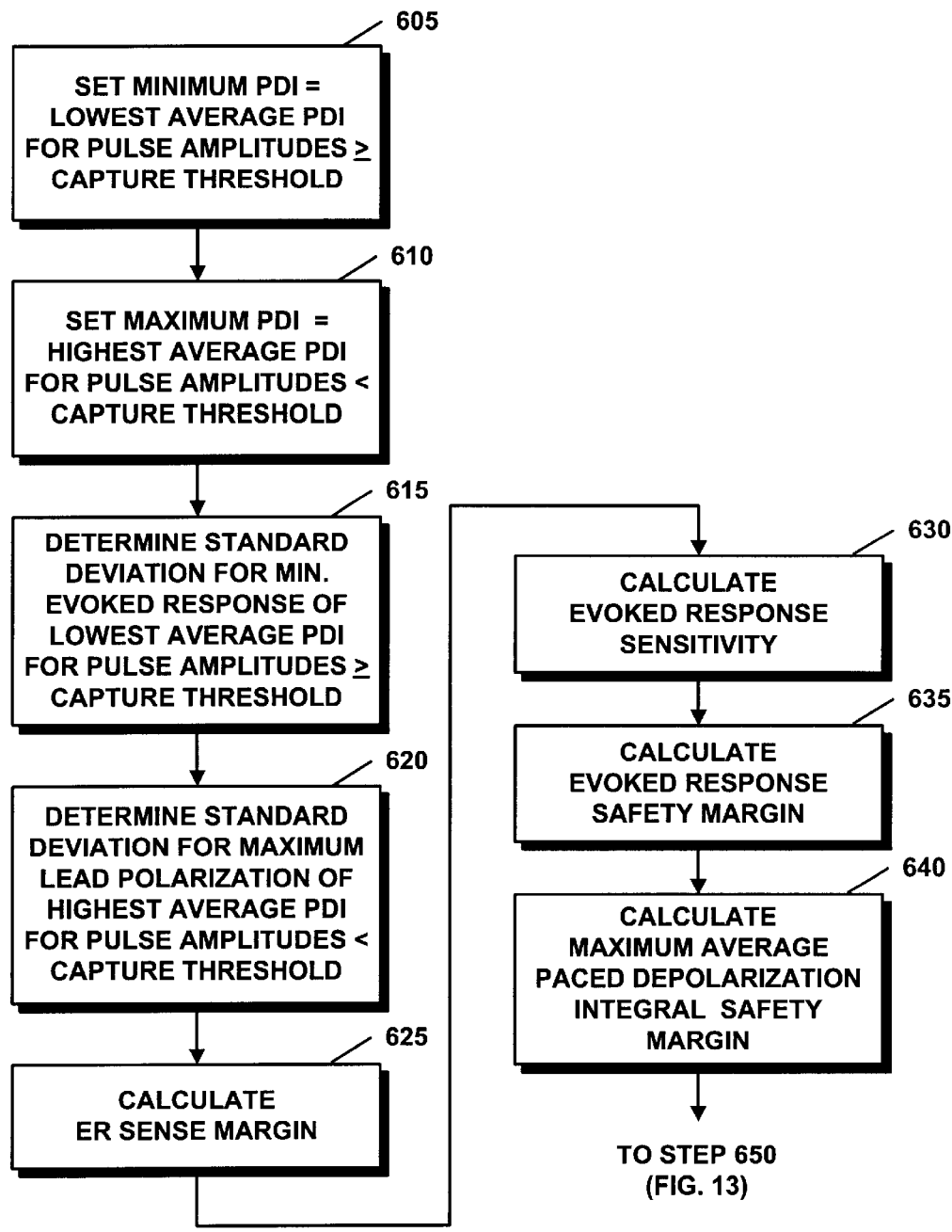
FIGS. 12 and 13 depict a flow chart describing a method used in the operation of FIG. 3 for mathematically analyzing the paced depolarization integral data to determine the feasibility of successfully performing automatic capture.
Figure 13:
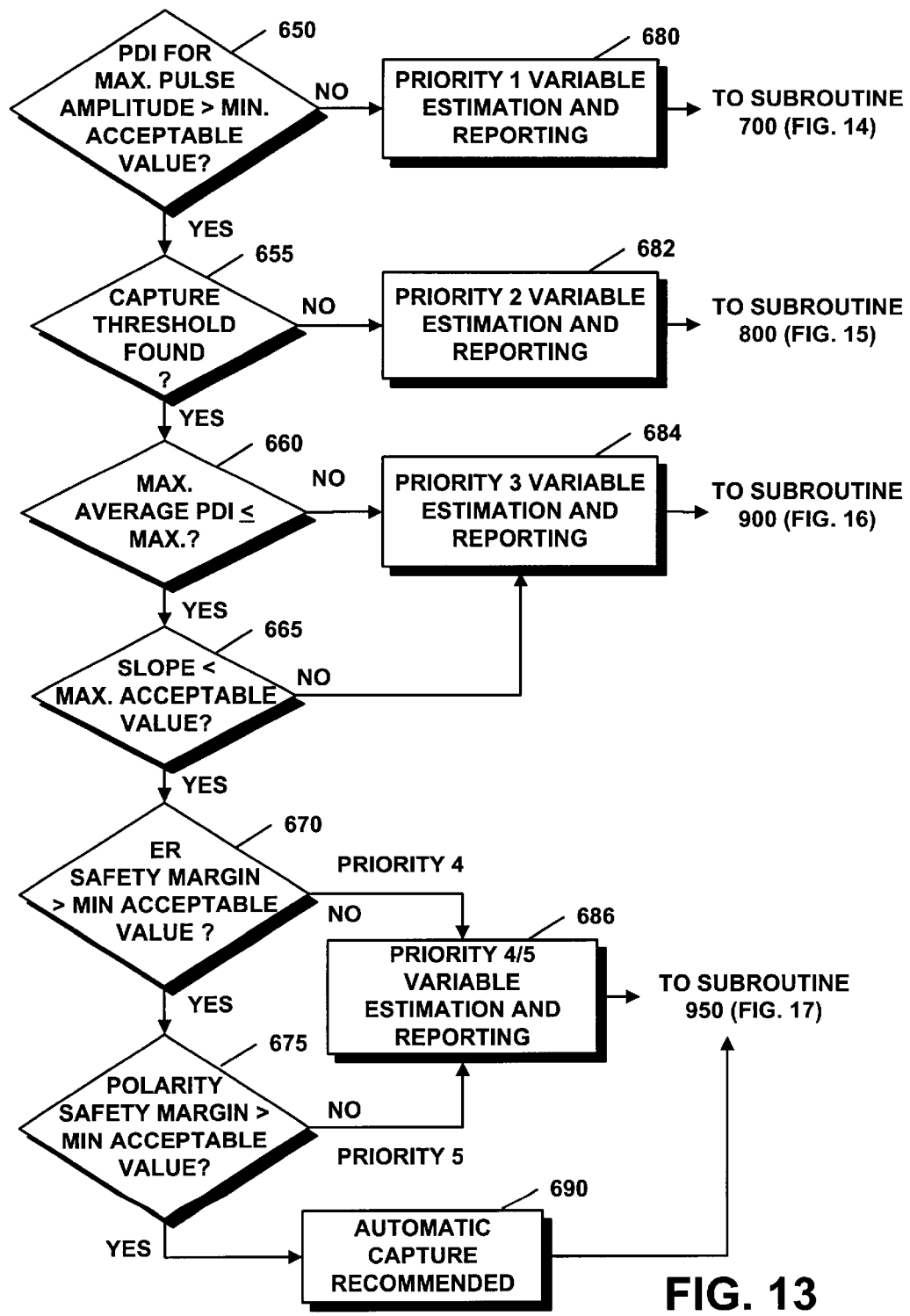

Having calculated the slope 930 and intercept 925, the calibration process 150 then proceeds to the automatic capture recommendation subroutine 600 of FIGS. 12 and 13. In FIGS. 12 and 13 a flow chart is shown depicting the details of one embodiment of the subroutine 600 called upon by the calibration process 150 for determining whether automatic capture is recommended.

In order for the calibration process 150 to determine that automatic capture is recommended, an evoked response sense margin is calculated and a series of pre-defined criteria are met. Starting at step 605 of FIG. 12, the minimum paced depolarization integral associated with an evoked response (ERMIN) is set as the lowest average paced depolarization integral determined in response to any pulse amplitude equal to, or exceeding the capture threshold.

At step 610, the maximum paced depolarization integral associated with only the lead polarization signal and not an evoked response (POLMAX) is determined as the highest average paced depolarization integral (PDI) found for any pulse amplitude less than the capture threshold. For the sample data plotted in FIG. 11, the minimum evoked response (ERMIN) would be determined as the average paced depolarization integral corresponding to 4.5 Volts. The maximum lead polarization would be determined as the average paced depolarization integral corresponding to 0.5 Volt.

The difference between this minimum evoked response integral average (ERMIN) and the maximum lead polarization integral average (POLMAX) must be large enough to allow accurate discrimination between the two, i.e., between capture and non-capture. To evaluate whether this difference is large enough for reliable capture detection, an evoked response (ER) sense margin is calculated based on statistical methods used within the field of transmission theory. In order to make this evaluation, the standard deviations of the minimum evoked response and maximum lead polarization should also be known. Hence, at step 615, the standard deviation of the minimum evoked response (SD_ERMIN) is set equal to the standard deviation of the lowest average paced depolarization integral (PDI) found for all pulse amplitudes equal to, or greater than the capture threshold (ERMIN).

Likewise, at step 620, the standard deviation for the maximum lead polarization (SD_POLMAX) is set equal to the standard deviation (SD) of the highest average paced depolarization integral found for all pulse amplitudes less than the capture threshold (POLMAX).

Having determined the average and standard deviation of the minimum evoked response (ERMIN) integral and the maximum lead polarization (POLMAX) integral, the evoked response (ER) sense margin is calculated at step 625, for example according to the following equation:

ER Sense Margin=(ERMIN−2.$SD\_$ERMIN)−(POLMAX+2.$SD\_$POLMAX), wherein:
ERMIN is the minimum average paced depolarization integral for all capturing pulse amplitudes;
SD_ERMIN is the standard deviation of ERMIN;
POLMAX is the maximum average paced depolarization integral for all non-capturing pulse amplitudes; and
SD_POLMAX is the standard deviation of POLMAX.

Figure 18:
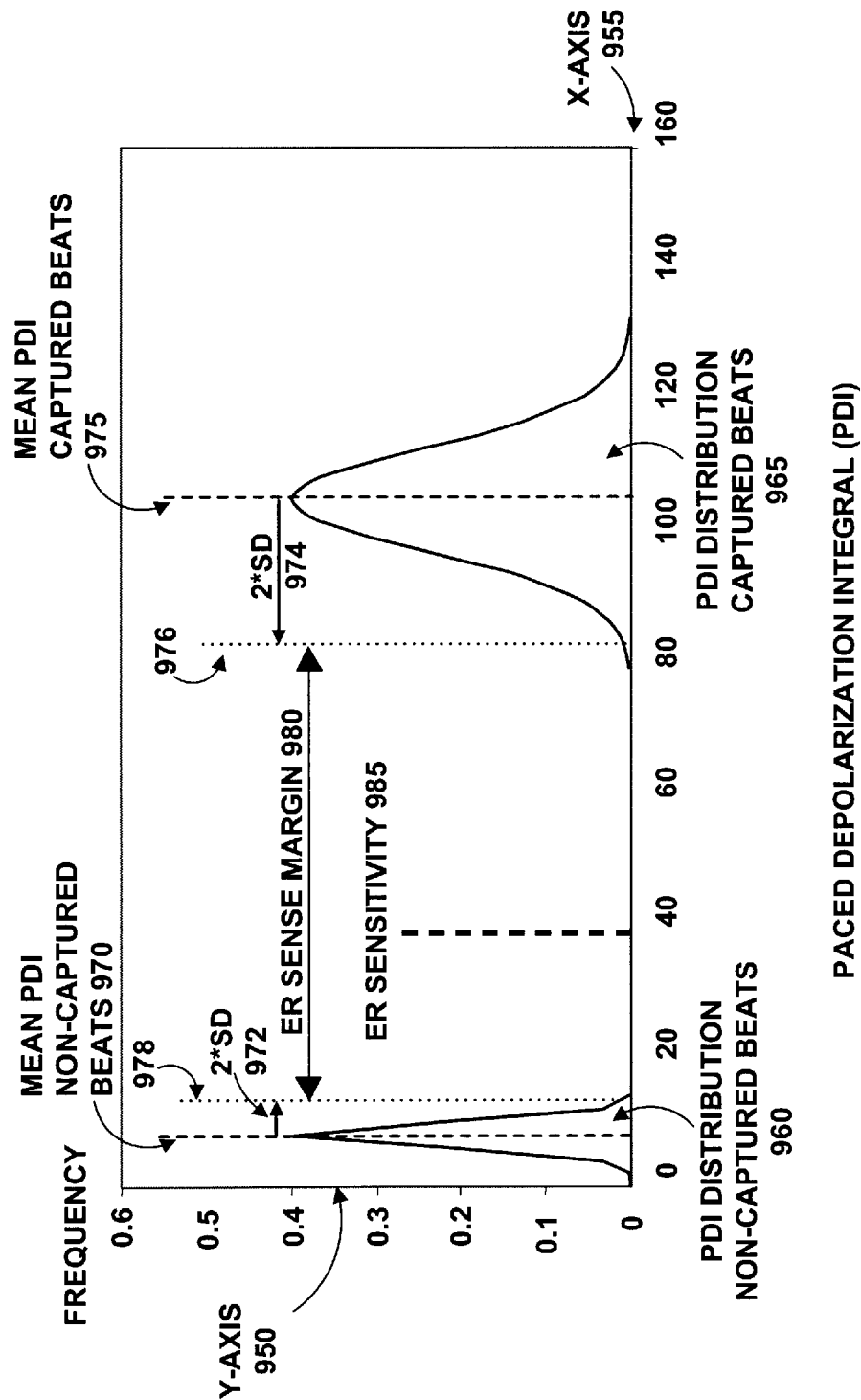
FIG. 18 is a frequency distribution plot of paced depolarization integral data collected according to the method of FIG. 8, illustrating the statistical basis for determining if automatic capture should be recommended according to the method of FIGS. 12 and 13.

Referring to FIG. 18, it illustrates graphically the rationale for the calculation of the evoked response (ER) sense margin (step 630). The frequency distribution of the paced depolarization integrals is plotted with frequency on the Y-axis 950 and paced depolarization integral (PDI) on the X-axis 955. Two distinct curves are observed, where the left-most curve 960 represents the occurrences of paced depolarization integrals at sub-threshold stimulation amplitudes (non-capture), and the right-most curve 965 represents the occurrences of paced depolarization integrals during capture stimulation. The paced depolarization integrals making up the left curve 960 represent only the lead polarization signal. The paced depolarization integrals making up the right curve 965 represents the evoked response plus the lead polarization signal.

The mean 975 of the captured paced depolarization integrals less two standard deviations 974 of the mean is indicated by the dashed line 976, and this value represents the first parenthetical term, (ERMIN−2·SD_ERMIN), in the equation above. The second parenthetical term, (POLMAX−2·SD_POLMAX), in the above equation is indicated by the dashed line 978, which represents the mean 970 of the paced depolarization integrals during non-capture stimulation plus two standard deviations 972 of the mean.

The difference between these two values 976 and 978 represents the evoked response sense margin 980. The evoked response sense margin is calculated conservatively by using the minimum average evoked response (ERMIN) integral and the maximum lead polarization (POLMAX) integral in above equation rather than the overall average evoked response integral and the overall average lead polarization integral. Referring back to FIG. 12, the evoked response sensitivity (ER SENSITIVITY) is calculated next at step 630 according to the following equation:

$$ER\ SENSITIVITY = 0.333 \cdot (ER\ SENSE\ MARGIN) + POLMAX + 2 \cdot SD\_POLMAX,$$

where:
ER SENSE MARGIN is found from the "ER Sense Margin" equation above;
POLMAX is the maximum average paced depolarization integral for all non-capturing pulse amplitudes; and
SD_POLMAX is the standard deviation of POLMAX.

The evoked response sensitivity (ER SENSITIVITY) is indicated by the heavy dashed line 985 in FIG. 18. The evoked response sensitivity setting is set at one-third of the way between the lower and upper boundaries 978 and 976, respectively, of the evoked response (ER) sense margin 980. When automatic capture is enabled, any paced depolarization integral that exceeds this evoked response (ER) sensitivity level 985 will be detected as capture. The evoked response (ER) sensitivity 985 is set closer to the maximum average lead polarization integral (POLMAX) than the minimum average evoked response integral (ERMIN) because during unipolar stimulation, the evoked response is expected to be variable while the polarization signal is known to be relatively stable.

Referring to step 635 of FIG. 12, the evoked response safety margin is calculated according to the following equation:

$$ER\ SAFETY\ MARGIN = (ERMIN)/(ER\ SENSITIVITY),$$

where:
ERMIN is the minimum average paced depolarization integral for all capturing pulse amplitudes; and
ER SENSITIVITY is determined from the ER SENSITIVITY equation above.

At step 640, the lead polarization safety margin is calculated according to the following equation:

$$POL\ SAFETY\ MARGIN = (ER\ SENSITIVITY)/(POLMAX),$$

where:
POLMAX is the maximum average paced depolarization integral for all non-capturing pulse amplitudes; and
ER SENSITIVITY is found from the ER SENSITIVITY equation above.

These safety margins provide a measure of performance of the automatic capture algorithm in terms of signal to noise, so that the physician can be assured that the system will perform adequately and safely. After calculating the safety margins, subroutine 600 continues to step 650 of FIG. 13. In FIG. 13, decision steps 650 through 675 represent the criteria that are to be met for automatic capture to be recommended. At decision step 650, the average paced depolarization integral (PDI) calculated for the maximum pulse amplitude tested, 4.5 Volts in the present example, must equal or exceed a minimum (MIN) acceptable value, preferably a value of 180. If this criterion is not met, automatic capture is not feasible because the evoked response signal is likely too small. Subroutine 600 indicates a "Priority 1" calibration variable estimation and reporting at step 680. Calibration process 150 then continues by calling upon subroutine 700 to calculate the calibration variable estimates and report their values as will be further described in conjunction with FIG. 14.

At decision step 655, subroutine 600 recalls whether the capture threshold was found or if the 0 Voltage level was reached during the capture search of subroutine 500 (FIG. 9) before detecting the capture threshold. If a capture threshold was not identified, automatic capture is not feasible because either the evoked response signal was insufficient or the lead polarity signal was too large to allow recognition of capture. A high slope indicates that polarization is a large negative voltage that increases with the pulse voltage. At high pulse voltage, polarization could be indistinguishable from the evoked response and non-capture or capture could have a similar appearance.

Subroutine 600 indicates "Priority 2" calibration variable estimation and reporting at step 682. Calibration process 150 then continues by calling upon subroutine 800 to calculate calibration variable estimates and report their values as will be further described in conjunction with FIG. 15.

At decision step 660, the subroutine 600 compares the maximum average paced depolarization integral found for non-capturing pulse amplitudes (POLMAX) to a maximum (MAX) acceptable value, preferably a value of 250. If this criterion is not met, automatic capture is not feasible because the lead polarity signal is too large. Subroutine 600 indicates "Priority 3" calibration variable estimation and reporting at step 684. Calibration process 150 then continues by calling upon subroutine 900 to calculate calibration variable estimates and to report their values as it will be described in conjunction with FIG. 16.

At decision step 665, subroutine 600 compares the slope of the response curve to a maximum (MAX) acceptable value, preferably a value of 30. If this criterion is not met, automatic capture is not feasible because the lead polarity signal is too large. A high slope indicates that the response curve is more closely related to the stimulation pulse amplitude, due to lead polarization, rather than the evoked response making automatic capture less reliable. Subroutine 600 indicates "Priority 3" calibration variable estimation and reporting at step 684. Calibration process 150 then continues by calling upon subroutine 900 to calculate calibration variable estimates and report their values as will be described in conjunction with FIG. 16.

At decision step 670, subroutine 600 compares the evoked response (ER) safety margin to a minimum acceptable value, preferably a value of 1.5:1. If this criterion is not met, automatic capture is not feasible because of inadequate signal to noise quality. Subroutine 600 indicates "Priority 4" calibration variable estimation and reporting at step 686. Calibration process 150 then continues by calling upon subroutine 950 to calculate calibration variable estimates and report their values as will be described in conjunction with FIG. 17.

At decision step 675, the subroutine 600 compares the polarization safety margin to a minimum acceptable value, preferably a value of 1.333. If this criterion is not met, automatic capture is not feasible for the same reason stated above as in decision step 670. Subroutine 600 indicates "Priority 5" calibration variable estimation and reporting at step 686. Calibration process 150 then continues by calling upon subroutine 700 to calculate calibration variable estimates and report their values as will be described in conjunction with FIG. 17.

If all the criteria of decision steps 650 through 675 are met, automatic capture is recommended. Subroutine 600 indicates that automatic capture is recommended at step 690. Calibration process 150 then continues by calling upon subroutine 700 to calculate calibration variable estimates and report their values as will be described in conjunction with FIG. 17.

Even if any of the criteria tested in decision steps 650 through 675 are not met so that automatic capture is not recommended, the medical practitioner still has the option to enable automatic capture. Therefore, calibration variable estimates are still calculated and reported according to the priority indicated in FIG. 13.

The following automatic capture calibration variables are estimated and reported: 1) maximum evoked response, 2) minimum evoked response, 3) polarization, 4) evoked response sensitivity, 5) evoked response safety margin, and 5) polarization safety margin. However, the calibration variable estimates are calculated differently depending on which criterion of subroutine 600 was not satisfied. Knowing the estimates of these variables, the medical practitioner can make appropriate selections in programming the automatic capture feature.

Figure 14:
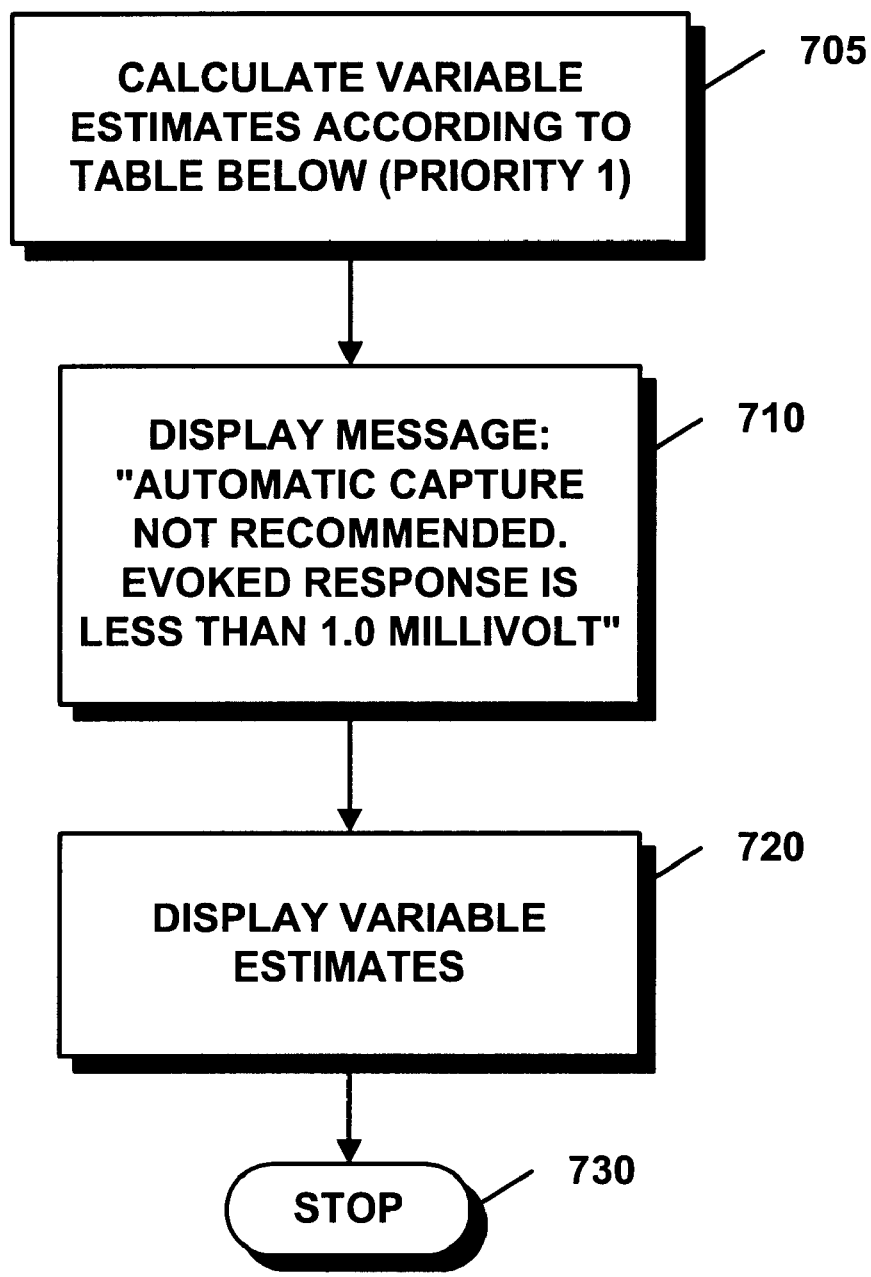
FIGS. 14 through 17 depict methods or subroutines used in the operation of FIG. 3 for estimating calibration variables to be displayed as programming information for the medical practitioner.

In FIGS. 14 through 17, a series of flow charts is shown depicting the details of one embodiment of subroutines 700, 800, 900, 950, respectively, called upon by the calibration process 150 for calculating and reporting the calibration variable estimates and displaying the automatic capture recommendation information. Referring to FIG. 14, if subroutine 600 of FIGS. 12 and 13, determines that automatic capture is not recommended according to Priority "1" due to the average pacing depolarization integral at the maximum stimulation amplitude being too low (decision step 650, FIG. 13). The calibration variable estimates are calculated at step 705 of FIG. 14 according to the Priority "11" equations shown in the Table III below.

TABLE III

Priority 1 Variable Estimation Calculations

| VARIABLE | EQUATION |
| --- | --- |
| MAXIMUM EVOKED RESPONSE (MILLIVOLTS)= | MAXIMUM PACED DEPOLARIZATION INTEGRAL AT 4.5 VOLTS / (18 * GF) |
| MINIMUM EVOKED RESPONSE (MILLIVOLTS) = | MINIMUM PACED DEPOLARIZATION INTEGRAL AT 4.5 VOLTS / (18 * GF) |
| POLARIZATION (MILLIVOLTS) = | MAXIMUM PACED DEPOLARIZATION INTEGRAL AT 0 VOLT / (18 * GF) |
| ER SENSITIVITY = | 0.333* (MIN EVOKED RESPONSE − POLARIZATION) + POLARIZATION |
| ER SAFETY MARGIN = | MIN EVOKED RESPONSE / ER SENSITIVITY |
| POLARIZATION SAFETY MARGIN = | ER SENSITIVITY / POLARIZATION |

A message indicating the automatic capture is not recommended because the evoked response is less than 1.0 millivolt is displayed on display 107 at step 710, and the calibration variable estimates are displayed at step 720. The automatic capture calibration process 150 is thus complete and terminated at step 730.

In this "Priority 1" situation, the maximum evoked response is calculated as the maximum paced depolarization integral that occurred at the maximum pulse amplitude tested (4.5 Volts in the present example) as shown in the Table III. The pacing depolarization integral values for the maximum evoked response, minimum evoked response, and polarization are converted to units of millivolts by dividing by a constant, in this example 18, and a gain factor which depends on the gain setting used by ventricular sensing circuit 84.

The minimum evoked response is calculated as the minimum paced depolarization integral occurring at the maximum pulse amplitude tested, preferably 4.5 Volts, and converted to millivolts by dividing by the appropriate conversion factors. The polarization signal is estimated as the maximum paced depolarization integral occurring at 0 Volt pulse amplitude and is converted to millivolts. Since the evoked response is determined as being too low to recommend automatic capture, these estimates report the minimum evoked response and polarization signals at levels that indicate the smallest difference that can be expected to occur between the evoked response and the lead polarization signal. The evoked response (ER) sensitivity, evoked response (ER) safety margin and polarization safety margin are calculated as indicated in Table III. The ER sensitivity is effectively set more sensitive in this case where the evoked response signal is expected to be difficult to distinguish from the polarization signal.

Figure 15:
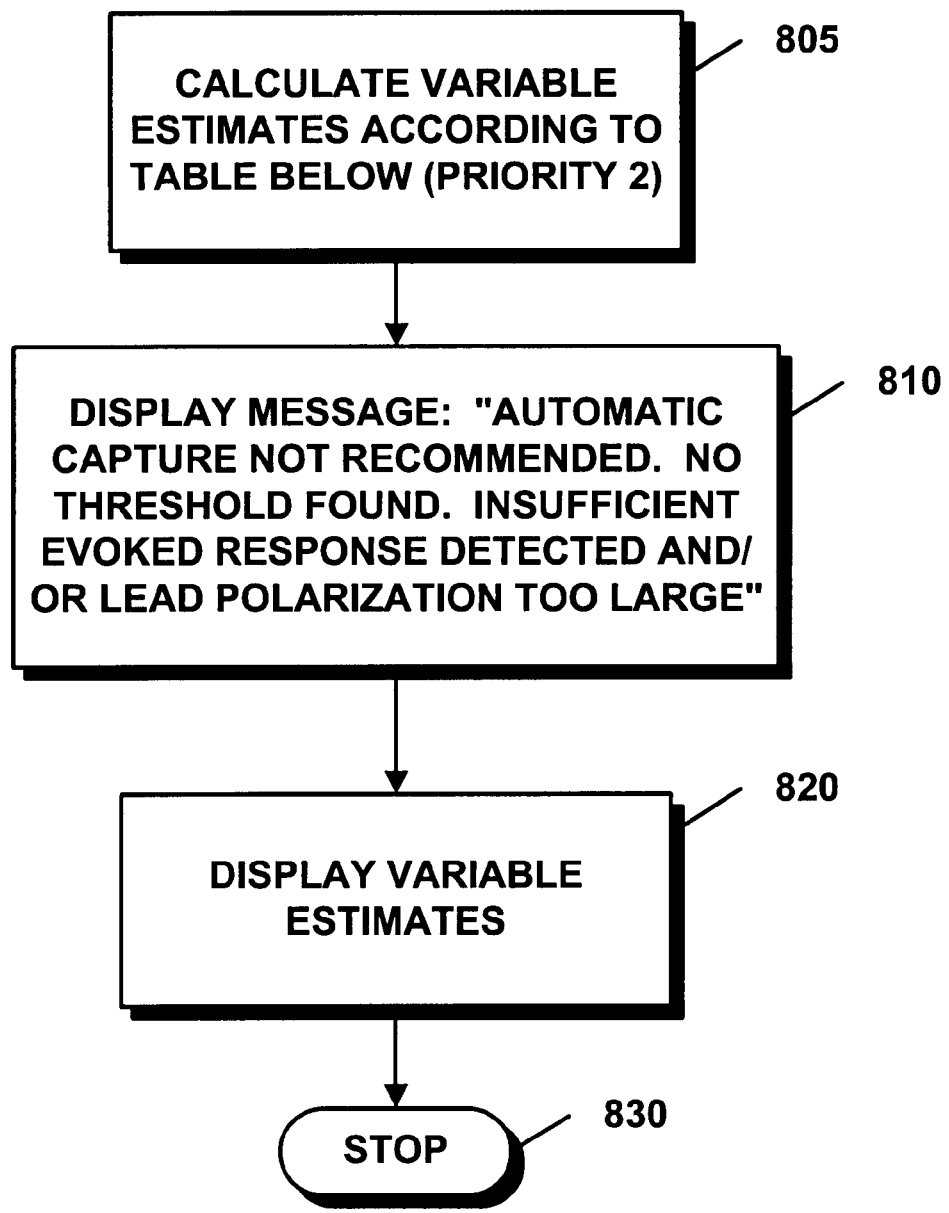

Referring to FIG. 15, if subroutine 600 determines that automatic capture is not recommended according to Priority "2" due to the capture threshold not being found (decision step 655 of FIG. 13), the calibration variable estimates are calculated at step 705B according to the Priority "2" equations shown in the following Table IV.

TABLE IV

Priority 2 Variable Estimation Calculations

| VARIABLE | EQUATION |
| --- | --- |
| MAXIMUM EVOKED RESPONSE (MILLIVOLTS) = | MAXIMUM PACED DEPOLARIZATION INTEGRAL AT 4.5 VOLTS / (18 * GAIN FACTOR) |
| MINIMUM EVOKED RESPONSE (MILLIVOLTS) = | MINIMUM PACED DEPOLARIZATION INTEGRAL AT 4.5 VOLTS / (18 * GAIN FACTOR) |
| POLARIZATION (MILLIVOLTS) = | MAXIMUM PACED DEPOLARIZATION INTEGRAL AT 0 VOLT / (18 * GAIN FACTOR) |
| ER SENSITIVITY = | 0.333* (MINIMUM EVOKED RESPONSE − POLARIZATION) + POLARIZATION |
| ER SAFETY MARGIN = | MINIMUM EVOKED RESPONSE / ER SENSITIVITY |
| POLARIZATION SAFETY MARGIN = | ER SENSITIVITY / POLARIZATION |

The message indicating that automatic capture is not recommended because the capture threshold was not found due to either insufficient evoked response detection and/or too high of lead polarization signal is displayed on display 107 at step 810, and the calibration variable estimates are displayed at step 820. The maximum and minimum evoked responses are calculated in the same way as in Priority "1" estimations when the evoked response was also considered insufficient. In this "Priority 2" case where lead polarization is considered too large, the polarization signal is reported as the maximum paced depolarization integral found for 3.5 Volts pulse amplitude, so that the polarization signal estimate is reported as being very high, thus reducing the possibility of inappropriate automatic capture programming.

The evoked response sensitivity, the evoked response safety margin and the polarization safety margin are calculated in the same was as Priority "1" estimations. At step 830, the calibration process 150 is terminated.

Figure 16:
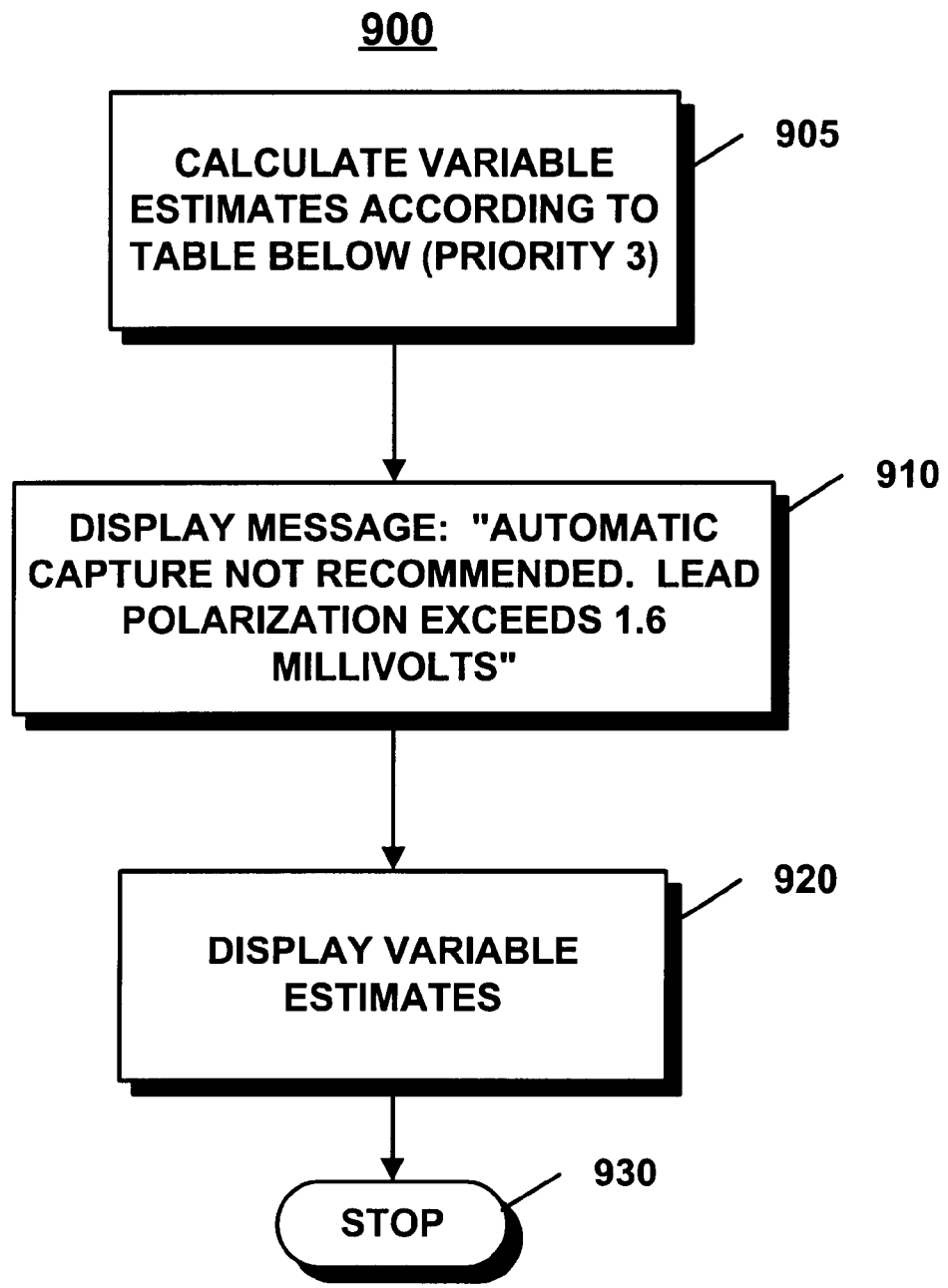

Referring to FIG. 16, if subroutine 600 determines that automatic capture is not recommended according to Priority "3" due to either too high of polarization signal or too high of slope of the stimulation response curve (decision steps 660 and 665, respectively, FIG. 13), the calibration variable estimates are calculated at step 905 according to the Priority "3" equations shown in the Table V below.

TABLE V

Priority 3 Variable Estimation Calculations

| VARIABLE | EQUATION |
| --- | --- |
| MAXIMUM EVOKED RESPONSE (MILLIVOLTS) = | (MAXIMUM PDI AT CAPTURE THRESHOLD − MINIMUM PDI AT 1.0 VOLTS BELOW CAPTURE THRESHOLD) / (18 * GAIN FACTOR) |
| MINIMUM EVOKED RESPONSE (MILLIVOLTS) = | AVERAGE PDI AT CAPTURE THRESHOLD − AVERAGE PDI AT 1.0 VOLTS BELOW CAPTURE THRESHOLD / (18 * GAIN FACTOR) |
| POLARIZATION (MILLIVOLTS) = | MAXIMUM PDI AT 4.5 VOLTS − (18 * GAIN FACTOR *MINIMUM EVOKED RESPONSE) / (18 * GAIN FACTOR) |
| ER SENSITIVITY = | 0.333* (MINIMUM PDI AT 4.5 VOLTS − MAXIMUM PDI AT 3.5 VOLTS) + MAXIMUM PDI AT 3.5 VOLTS |
| ER SAFETY MARGIN = | MINIMUM EVOKED RESPONSE / ER SENSITIVITY |
| POLARIZATION SAFETY MARGIN = | ER SENSITIVITY / POLARIZATION |

The message indicating that automatic capture is not recommended because the lead polarization exceeds 1.6 millivolts is displayed on display 107 at step 910, and the calibration variable estimates are displayed at step 920. At step 930, the calibration process 150 is terminated.

In this case where lead polarization is considered too large, the polarization signal is reported as the maximum paced depolarization integral found for 4.5 Volts pulse amplitude so that the polarization signal estimate is reported as being very high thus preventing inappropriate automatic capture programming. The evoked response signal in this case is considered normal but the paced depolarization integral associated with the evoked response will be high due to the contribution of the high polarization signal.

Therefore, the maximum evoked response is estimated as the maximum paced depolarization integral found at the capture threshold minus the minimum paced depolarization integral at 1.0 Volt below the capture threshold. The minimum evoked response is estimated as the average paced depolarization integral at the capture threshold minus the average paced depolarization integral at 1.0 Volt below the capture threshold.

The large effect of the polarization signal is thus subtracted from the paced depolarization integrals at capture to estimate the maximum and minimum evoked response signals. The evoked response sensitivity is estimated to be a low sensitivity (high setting) based on the maximum paced depolarization integral occurring at 3.5 Volts plus one third of the difference between this integral and the minimum paced depolarization integral at 4.5 Volts. By setting the sensitivity high, the high polarization signal may not be detected as capture. The evoked response safety margin and the polarization safety margin are calculated as indicated in Table V.

Figure 17:
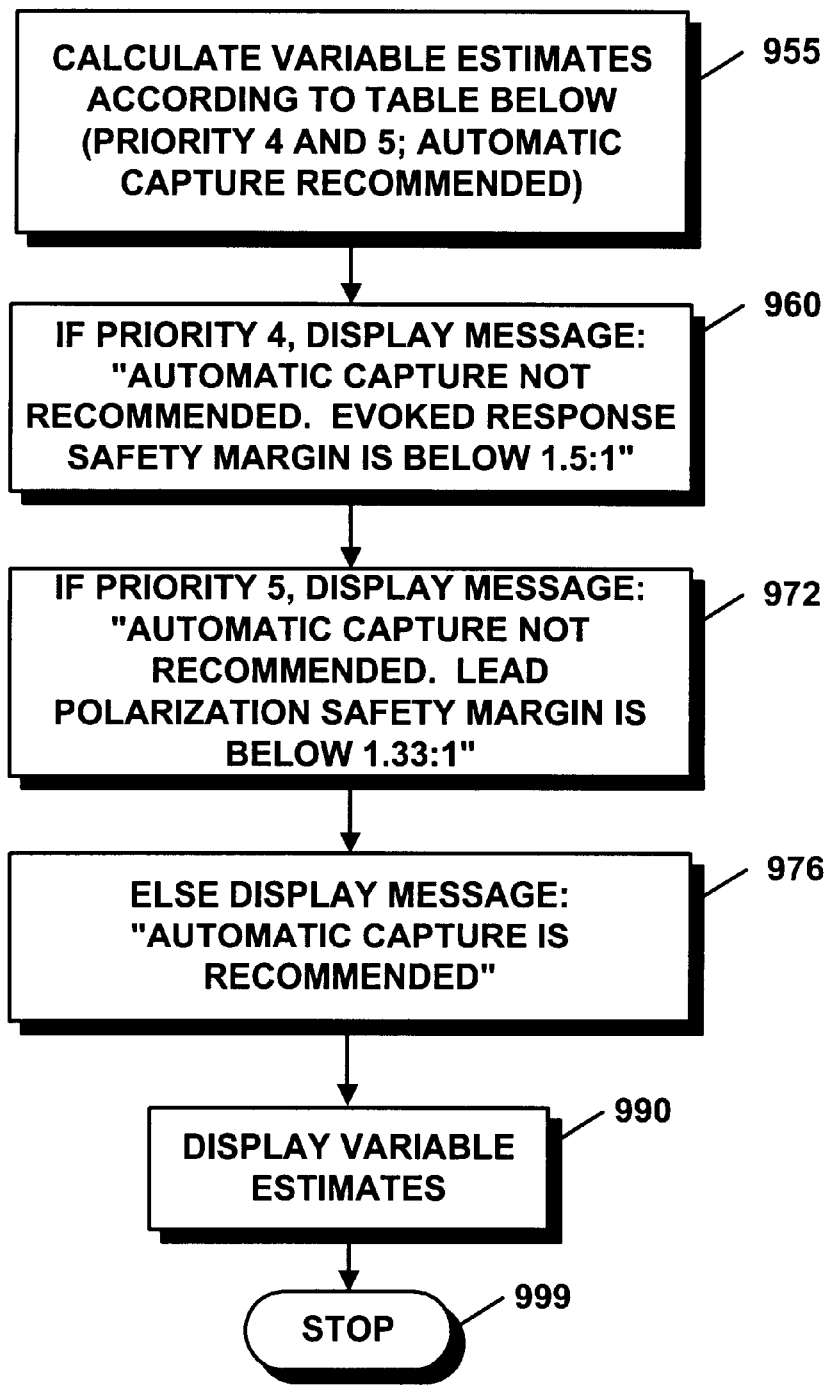

Referring to the subroutine 950 of FIG. 17, if subroutine 600 determines that automatic capture is not recommended due to a low evoked response safety margin or a low polarization safety margin (decision steps 670 and 675, respectively, FIG. 13), or if automatic capture is found to be recommended (step 690 FIG. 13), the calibration variable estimates are calculated at step 905 according to the Priority "4" and Priority "5" equations shown in the Table VI below.

TABLE VI

Priority "4" or "5" and "Automatic Capture Recommended" Variable Estimation Calculations

| VARIABLE | EQUATION |
| --- | --- |
| MAXIMUM EVOKED RESPONSE (MILLIVOLTS) = | (MAXIMUM PDI AT OR ABOVE CAPTURE THRESHOLD) / (18 * GAIN FACTOR) |
| MINIMUM EVOKED RESPONSE (MILLIVOLTS) = | (MINIMUM PDI AT OR ABOVE CAPTURE THRESHOLD) / (18 * GAIN FACTOR) |
| POLARIZATION (MILLIVOLTS) = | (MAXIMUM AVERAGE PDI BELOW CAPTURE THRESHOLD) / (18 * GAIN FACTOR) |
| ER SENSITIVITY = | 0.333* (ER SENSE MARGIN) + POLARIZATION + 2 * SD_POLMAX |
| ER SAFETY MARGIN = | MINIMUM EVOKED RESPONSE / ER SENSITIVITY |
| POLARIZATION SAFETY MARGIN = | ER SENSITIVITY / POLARIZATION |

If the evoked response safety margin is too low, a message is displayed on display 107 at step 960 indicating that automatic capture is not recommended because the evoked response safety margin is below 1.5:1. If the polarization safety margin is too low, a message is displayed on display 107 at step 972 indicating that automatic capture is not recommended because the polarization safety margin is below 1.33:1. If all criteria of decision steps 650 through 675 are met, a message is displayed on display 107 at step 976 indicating that automatic capture is recommended. The calibration variable estimates are then displayed at step 990, and the automatic capture calibration process 150 is thus complete and terminated at step 999.

For these cases, the maximum and minimum evoked responses are estimated as the actual maximum and the actual minimum paced depolarization integrals occurring in response to pulse amplitudes at or above the capture threshold as indicated in Table VI. The polarization signal is estimated as the actual maximum average paced depolarization integral in response to any pulse amplitude below the capture threshold.

The evoked response sensitivity, evoked response safety margin, and polarization safety margin are calculated in the same way as previously described during subroutine 600 (step 630, 635, and 640, FIG. 12). The details of these calculations are also shown in Table VI.

Thus, a paced depolarization integral method for calibrating automatic capture has been described for application in unipolar sensing configurations in the ventricular chambers of the heart. This method determines the margin between the evoked response and the lead polarization signal and whether these signals can be safely discriminated. This method thus determines if automatic capture can be safely recommended. This method further reports pertinent calibration variables valuable to a medical practitioner in making decisions whether to enable the automatic capture feature in a given patient and, if so, in selecting automatic capture operating parameters.

While the invention herein disclosed has been described according to specific embodiments and applications thereof, numerous modifications and variations could be made thereto by those skilled in the art without departing from the scope of the invention.

What is claimed is:

1. A method of calibrating an automatic capture verification feature for use in an implantable cardiac stimulation device, comprising:
   collecting cardiac signal data and calculating a paced depolarization integral, for a plurality of stimulation output settings;
   determining a capture detection threshold; and
   comparing the capture detection threshold to a computed value based on the paced depolarization integral, for determining if automatic capture verification is recommended.

2. The method of claim 1, wherein the step of collecting cardiac signal data includes collecting cardiac signal data for an output setting for an evoked response at which capture occurs, and at least one output setting at which loss of capture occurs.

3. The method of claim 2, wherein the step of determining the capture detection threshold includes using a unipolar or bipolar electrode configuration.

4. The method of claim 2, wherein the step of determining the capture detection threshold includes setting a temporary capture detection threshold.

5. The method of claim 4, wherein the step of setting the temporary capture detection threshold includes calculating the temporary capture detection threshold as a sum of an average characteristic value for a minimum stimulation output plus half the difference between an average characteristic value for a maximum stimulation output and an average characteristic value for a minimum stimulation output.

6. The method of claim 4, wherein the step of setting the temporary capture detection threshold includes determining the difference between a characteristic value for sequentially decreasing stimulation output settings.

7. The method of claim 6, wherein the step of setting the temporary capture detection threshold includes determining capture threshold as a lowest output setting at which the difference between an average characteristic value and the average characteristic value for the next lower stimulation output setting equals or exceeds a temporary capture detection threshold.

8. The method of claim 2, wherein the step of collecting the paced depolarization integral includes sampling a cardiac signal following the delivery of a stimulation pulse.

9. The method of claim 8, wherein the step of collecting the paced depolarization integral further includes integrating a sampled cardiac signal following the delivery of the stimulation pulse to obtain a paced depolarization integral for the sampled cardiac signal.

10. The method of claim 9, wherein the step of collecting the paced depolarization integral further includes setting an integration window following the delivery of the stimulation pulse during which signal samples are integrated.

11. The method of claim 10, wherein the step of integrating the sampled cardiac signal includes integrating only negative signal samples.

12. The method of claim 11, wherein the step of integrating the sampled cardiac signal includes integrating only negative signal samples less than an integration baseline.

13. The method of claim 12, wherein integrating only negative signal samples less than the integration baseline includes determining the integration baseline by averaging a specified number of signal samples.

14. The method of claim 12, wherein integrating only negative signal samples less than the integration baseline includes determining the integration baseline by averaging a number of signal samples occurring relative to a post-pulse fast recharge period.

15. The method of claim 2, wherein the step of collecting cardiac signal data includes collecting characteristic values of cardiac signals for each of a predetermined number of stimulation pulses, at each of a predetermined number of stimulation output settings.

16. The method of claim 15, further including statistically analyzing the characteristic values for each of the stimulation output settings.

17. The method of claim 16, wherein the step of statistically analyzing includes determining an average and standard deviation of a characteristic value for each of the stimulation output settings.

18. The method of claim 17, further including storing the average characteristic cardiac signal value and the standard deviation for each of the stimulation output settings.

19. The method of claim 2, wherein the step of collecting cardiac signal data includes automatically adjusting a gain setting.

20. The method of claim 19, wherein the step of automatically adjusting the gain setting includes adjusting the gain until a cardiac signal amplitude reaches a signal amplitude criterion.

21. The method of claim 20, wherein the step of automatically adjusting the gain setting includes adjusting the gain until the cardiac signal amplitude reaches a predetermined maximum amplitude value.

22. The method of claim 20, further including aborting the method of calibrating when a gain cannot be adjusted to meet the signal amplitude criterion.

23. The method of claim 1, wherein the step of collecting cardiac signal data includes automatically adjusting a fusion avoidance parameter.

24. The method of claim 23, wherein the step of automatically adjusting the fusion avoidance parameter includes determining if fusion is suspected.

25. The method of claim 24, wherein the step of determining if fusion is suspected includes determining a cardiac signal variability.

26. The method of claim 25, wherein the step of determining the cardiac signal variability includes determining a standard deviation of an average characteristic value of the cardiac signal.

27. The method of claim 25, wherein determining the cardiac signal variability includes determining a coefficient of variation defined as a quotient of a standard deviation of an average characteristic value divided by an average characteristic value for a stimulation output setting.

28. The method of claim 25, wherein the step of determining the cardiac signal variability includes comparing the cardiac signal variability to a predetermined maximum value.

29. The method of claim 28, wherein if the cardiac signal variability exceeds a predetermined maximum value, suspecting fusion.

30. The method of claim 24, wherein the step of adjusting the fusion avoidance parameter includes increasing a base stimulation rate when fusion is suspected.

31. The method of claim 1, further comprising determining the plurality of variables relating to the automatic capture verification feature.

32. The method of claim 31, wherein the step of determining the plurality of variables relating to the automatic capture verification feature further includes determining a slope of a stimulation response curve defined by a relation between a number of average characteristic cardiac signal values and corresponding stimulation output settings.

33. The method of claim 31, wherein the step of determining the plurality of variables relating to the automatic capture verification feature further includes determining an intercept of a stimulation response curve.

34. The method of claim 31, wherein the step of determining the plurality of variables relating to the automatic capture verification feature further includes determining a set of calibration variables.

35. The method of claim 34, wherein the step of determining the set of calibration variables includes:
setting a minimum evoked response;
setting a maximum lead polarization;
setting an evoked response sensing margin;
setting an evoked response sensitivity;
setting an evoked response safety margin; and
setting a polarization signal safety margin.

36. The method of claim 35, wherein the step of setting the minimum evoked response includes setting a minimum average characteristic cardiac signal value for a stimulation output equal to or greater than a capture threshold.

37. The method of claim 35, wherein the step of setting the maximum lead polarization includes setting a maximum average characteristic cardiac signal value for a stimulation output less than a capture threshold.

38. The method of claim 35, wherein the step of setting the evoked response sensing margin includes setting a difference between a minimum evoked response less twice its standard deviation and a maximum lead polarization plus twice its standard deviation.

39. The method of claim 35, wherein the step of setting the evoked response sensitivity includes setting a sum of one-third of the evoked response sensing margin and a maximum lead polarization plus twice its standard deviation.

40. The method of claim 39, wherein the step of setting the evoked response sensitivity includes identifying a cardiac signal exceeding an evoked response sensitivity as a capture signal.

41. The method of claim 35, wherein the step of setting the evoked response safety margin includes setting a quotient of a minimum average evoked response divided by an evoked response sensitivity.

42. The method of claim 35, wherein the step of setting the polarization safety margin includes setting a quotient of an evoked response sensitivity divided by a maximum lead polarization.

43. The method of claim 35, further including the step of using a set of calibration variables for programming automatic capture operating parameters.

44. The method of claim 2, wherein the step of determining the plurality of variables further includes displaying a variable relating to the operation of automatic capture verification.

45. The method of claim 2, wherein the step of comparing the capture detection threshold includes comparing the capture detection threshold to an acceptable minimum value, so that automatic capture is not recommended if the capture detection threshold is less than an acceptable minimum value.

46. The method of claim 2, wherein the step of comparing the capture detection threshold to a predetermined value includes comparing a lead polarization to an acceptable maximum, so that automatic capture is not recommended if a lead polarization signal is greater than an acceptable maximum value.

47. The method of claim 2, further including the step of not recommending automatic capture if a capture threshold is not determined.

48. The method of claim 2, wherein the step of comparing the capture detection threshold to a predetermined value includes comparing an evoked response safety margin to a minimum acceptable value, so that automatic capture is not recommended if the evoked response safety margin is less than an acceptable minimum value.

49. The method of claim 2, wherein the step of comparing the capture detection threshold to a predetermined value includes comparing a polarization safety margin to a minimum acceptable value, so that automatic capture is not recommended if the polarization safety margin is less than an acceptable minimum value.

50. The method of claim 2, wherein the step of comparing the capture detection threshold to a predetermined value includes comparing a slope of a response curve to a maximum acceptable value, so that automatic capture is not recommended if the slope of the response curve is greater than an acceptable maximum value.

51. The method of claim 2, further including displaying a message indicating that automatic capture verification is recommended if at least one predefined condition is met.

52. The method of claim 51, further including displaying a message indicating that automatic capture verification is not recommended if the predefined condition is not met.

53. The method of claim 2, further including determining a first set of variables relating to the operation of automatic capture if automatic capture is recommended, and determining a second set of variables relating to the operation of automatic capture if automatic capture verification is not recommended.

54. The method of claim 53 further including a step of prioritizing a plurality of conditions required for recommending automatic capture verification.

55. The method of claim 54, further including displaying the first set of variables if automatic capture is recommended and displaying the second set of variables if automatic capture is not recommended.

56. A cardiac stimulation device capable of calibrating an automatic capture verification feature, comprising:
a pulse generator that selectively generates stimulation energy;
a lead, connected to the pulse generator, that delivers the stimulation energy to one or more cardiac chambers;
a sensing circuit, coupled to the lead, that collects cardiac signal data for a plurality of stimulation output settings;
a calculator that calculates paced depolarization integrals from the cardiac signal data;
a control circuit, connected to the sensing circuit, that determines a capture detection threshold; and
wherein the control circuit compares the capture detection threshold to a computed value based on the paced depolarization integral, for determining if automatic capture verification is recommended.

57. The cardiac stimulation device of claim 56, wherein the cardiac signal data include cardiac signal data collected for an output setting for an evoked response at which capture occurs, and for an output setting at which loss of capture occurs.

58. The cardiac stimulation device of claim 57, wherein the lead has a unipolar configuration.

59. The cardiac stimulation device of claim 57, wherein the paced depolarization integral includes samples of a cardiac signal that follows the delivery of a stimulation pulse.

60. The cardiac stimulation device of claim 59, wherein the paced depolarization integral includes integrated samples of a cardiac signal following the delivery of the stimulation pulse.

61. The cardiac stimulation device of claim 60, further including a timing circuit that sets an integration window following the delivery of the stimulation pulse during which signal samples are integrated.

62. The cardiac stimulation device of claim 61, wherein integrated samples of the cardiac signal include only integrated negative signal samples.

63. The cardiac stimulation device of claim 61, wherein integrated samples of the cardiac signal include only integrated negative signal samples less than an integration baseline.

64. The cardiac stimulation device of claim 63, wherein the control circuit determines an integration baseline by averaging a predetermined number of signal samples.

65. The cardiac stimulation device of claim 63, wherein the control circuit determines an integration baseline by averaging a number of signal samples occurring during a post-pulse fast recharge period.

66. A cardiac stimulation device capable of calibrating an automatic capture verification feature, comprising:

means for collecting cardiac signal data and for calculating a paced depolarization integral, for a plurality of stimulation output settings;

means for determining a capture detection threshold; and means for comparing the capture detection threshold to a computed value based on the paced depolarization integral, to determine if automatic capture verification is recommended.

67. The cardiac stimulation device of claim 66, wherein the cardiac signal data include cardiac signal data collected for an output setting for an evoked response at which capture occurs, and for an output setting at which loss of capture occurs.

68. The cardiac stimulation device of claim 67, further including means for delivering stimulation energy to one or more cardiac chamber having any of a unipolar configuration, a bipolar configuration, or a multipolar configuration.

69. The cardiac stimulation device of claim 68, wherein the paced depolarization integral includes samples of a cardiac signal that follows the delivery of a stimulation pulse.

70. The cardiac stimulation device of claim 69, wherein the paced depolarization integral includes integrated samples of a cardiac signal following the delivery of the stimulation pulse.

71. The cardiac stimulation device of claim 70, further including means for setting an integration window following the delivery of the stimulation pulse during which signal samples are integrated.

72. The cardiac stimulation device of claim 71, wherein integrated samples of the cardiac signal include only integrated negative signal samples less than an integration baseline.

73. The cardiac stimulation device of claim 72, wherein the integration baseline is determined by averaging a predetermined number of signal samples.

74. The cardiac stimulation device of claim 72, wherein the integration baseline is determined by averaging a plurality of signal samples that occur during a post-pulse fast recharge period.

* * * * *